United States Patent
Miyata et al.

(10) Patent No.: US 9,276,219 B2
(45) Date of Patent: Mar. 1, 2016

(54) MATERIAL FOR ORGANIC ELECTROLUMINESCENCE DEVICE AND ORGANIC ELECTROLUMINESCENCE DEVICE INCLUDING THE SAME

(71) Applicant: SAMSUNG DISPLAY CO., LTD., Yongin, Gyeonggi-Do (KR)

(72) Inventors: Yasuo Miyata, Yokohama (JP); Masatsugu Ueno, Yokohama (JP)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 0 days.

(21) Appl. No.: 14/576,779

(22) Filed: Dec. 19, 2014

(65) Prior Publication Data

US 2015/0179952 A1    Jun. 25, 2015

(30) Foreign Application Priority Data

Dec. 20, 2013   (JP) .................. 2013-264463

(51) Int. Cl.
| | | |
|---|---|---|
| *H01L 51/50* | (2006.01) | |
| *C07D 209/82* | (2006.01) | |
| *H01L 51/00* | (2006.01) | |
| *C07F 7/08* | (2006.01) | |
| *C07D 487/06* | (2006.01) | |

(52) U.S. Cl.
CPC .......... *H01L 51/0061* (2013.01); *C07D 487/06* (2013.01); *C07F 7/0812* (2013.01); *H01L 51/0072* (2013.01); *H01L 51/0073* (2013.01); *H01L 51/0094* (2013.01); *H01L 51/006* (2013.01); *H01L 51/0054* (2013.01); *H01L 51/0081* (2013.01); *H01L 51/5056* (2013.01); *H01L 51/5088* (2013.01); *H01L 2251/308* (2013.01)

(58) Field of Classification Search
None
See application file for complete search history.

(56) References Cited

U.S. PATENT DOCUMENTS

| | | | |
|---|---|---|---|
| 8,628,864 B2 | 1/2014 | Abe et al. | |
| 2007/0231503 A1 | 10/2007 | Hwang et al. | |
| 2012/0292576 A1* | 11/2012 | Parham et al. ............... | 252/500 |

FOREIGN PATENT DOCUMENTS

| | | |
|---|---|---|
| EP | 2 284 920 A1 | 2/2011 |
| JP | 2013-033804 A | 2/2013 |
| WO | WO 2010/110553 A2 | 9/2010 |
| WO | WO 2012/091471 A2 | 7/2012 |

* cited by examiner

*Primary Examiner* — Michael Barker
(74) *Attorney, Agent, or Firm* — Lee & Morse, P.C.

(57) ABSTRACT

A compound for an organic electroluminescence (EL) device is represented by the following Formula (1):

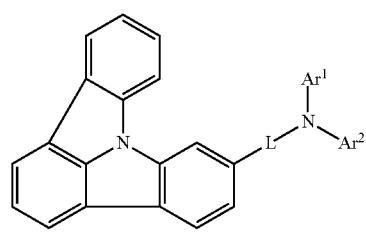

(1)

In Formula (1), $Ar^1$ and $Ar^2$ are independently a substituted or unsubstituted alkyl group, a substituted or unsubstituted aryl group, or a substituted or unsubstituted heteroaryl group, and L is a single bond, a substituted or unsubstituted arylene group, or a substituted or unsubstituted heteroarylene group.

12 Claims, 1 Drawing Sheet

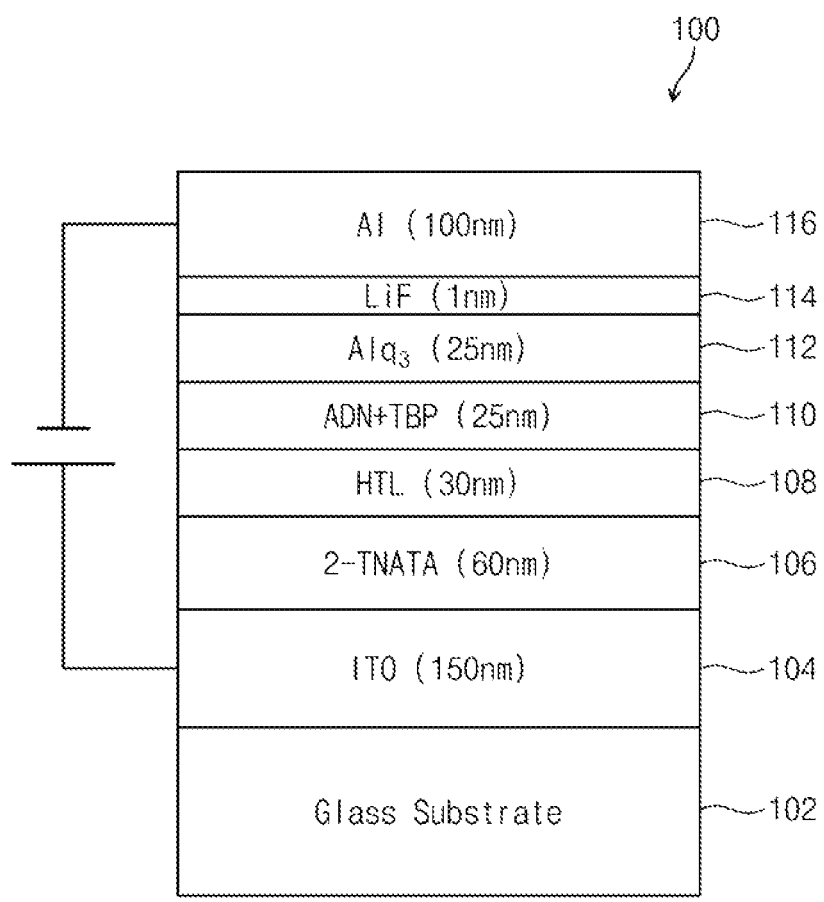

MATERIAL FOR ORGANIC ELECTROLUMINESCENCE DEVICE AND ORGANIC ELECTROLUMINESCENCE DEVICE INCLUDING THE SAME

CROSS-REFERENCE TO RELATED APPLICATION

Japanese Patent Application No. 2013-264463, filed on Dec. 20, 2013, in the Japanese Patent Office, and entitled: "Material for Organic Electroluminescence Device and Organic Electroluminescence Device Including the Same," is incorporated by reference herein in its entirety.

BACKGROUND

1. Field

Embodiments relate to a material for an organic electroluminescence device and an organic electroluminescence device including the same.

2. Description of the Related Art

In recent years, organic electroluminescence (EL) displays, which are one type of image display, have been actively developed. Unlike a liquid crystal display and the like, the organic EL display is so-called a self-luminescent display which recombines holes and electrons injected from an anode and a cathode in an emission layer to thus emit lights from a light-emitting material including an organic compound of the emission layer, thereby performing display.

SUMMARY

Embodiments are directed to a compound for an organic electroluminescence (EL) device, the compound being represented by the following Formula (1):

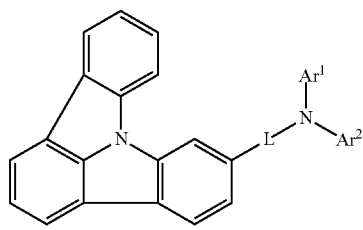

(1)

In Formula (1), $Ar^1$ and $Ar^2$ may independently be a substituted or unsubstituted alkyl group, a substituted or unsubstituted aryl group, or a substituted or unsubstituted heteroaryl group, and L is a single bond, a substituted or unsubstituted arylene group, or a substituted or unsubstituted heteroarylene group.

At least one of $Ar^1$ and $Ar^2$ may be a substituted or unsubstituted carbazolyl group, a substituted or unsubstituted dibenzofuryl group, or a substituted or unsubstituted dibenzothienyl group.

At least one of $Ar^1$ and $Ar^2$ may be a substituted or unsubstituted aryl group having 6 to 24 ring carbon atoms.

At least one of $Ar^1$ and $Ar^2$ may be a substituted or unsubstituted carbazolyl group, a substituted or unsubstituted dibenzofuryl group, or a substituted or unsubstituted dibenzothienyl group.

L may be a single bond or a substituted or unsubstituted arylene group having 6 to 18 ring carbon atoms.

Embodiments are also directed to a hole transport material including the compound represented by Formula (1).

Embodiments are also directed to an organic electroluminescence (EL) device including the compound represented by Formula (1) in a layer disposed between an emission layer and an anode.

BRIEF DESCRIPTION OF THE DRAWING

Features will become apparent to those of skill in the art by describing in detail example embodiments with reference to the attached drawing in which:

FIG. 1 illustrates a schematic diagram of an organic EL device 100 according to an example embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

According to an example embodiment, an organic EL device having high efficiency and long life may be manufactured by using an amine compound having an indolo[3,2,1-jk]carbazolyl group with high electron tolerance as a hole transport material of an organic EL device. In an example embodiment, high efficiency and long life of the organic EL device in a blue emission region and a green emission region may be realized by combining an amine with the indolo[3,2,1-jk]carbazolyl group at the position 6.

According to an example embodiment, a material for an organic EL device includes an amine compound represented by the following Formula (1).

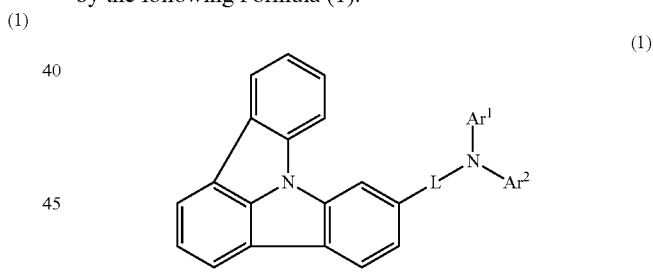

(1)

According to the present example embodiment, in Formula (1), $Ar^1$ and $Ar^2$ may independently be a substituted or unsubstituted alkyl group, a substituted or unsubstituted aryl group, or a substituted or unsubstituted heteroaryl group. L may be a single bond, a substituted or unsubstituted arylene group, or a substituted or unsubstituted heteroarylene group.

A substituted or unsubstituted alkyl group having 1 to 30 carbon atoms may be used for $Ar^1$ and $Ar^2$. Examples of the alkyl group include a methyl group, an ethyl group, a n-propyl group, an isopropyl group, a n-butyl group, a sec-butyl group, a t-butyl group, an i-butyl group, a 2-ethylbutyl group, a 3,3-dimethylbutyl group, a n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, a n-hexyl group, a 1-methylhexyl group, a 2-ethylhexyl group, a 2-butylhexyl group, a cyclohexyl group, a 4-methylcyclohexyl group, a 4-t-butylcyclohexyl group, a n-heptyl group, a 1-methylheptyl group, a 2,2-dimethylheptyl group, a 2-ethylheptyl group, a 2-butylheptyl group, a n-octyl group, a t-octyl group, a 2-ethyloctyl group, a 2-butyloctyl group, a 2-hexyloctyl group, a 3,7-dimethyloctyl group, a cyclooctyl group, a n-nonyl group, a n-decyl group, an adamantly group, a 2-ethyldecyl group, a 2-butyldecyl group, a 2-hexyldecyl group, a 2-octyldecyl group, a n-undecyl group, a n-dodecyl group, a 2-ethyldocecyl group, a 2-butyldodecyl group, a 2-hexyldodecyl group, a 2-octyldodecyl group, a n-tridecyl group, a n-tetradecyl group, a n-pentadecyl group, a n-hexadecyl group, a 2-ethylhexadecyl group, a 2-butylhexadecyl group, a 2-hexylhexadecyl group, a 2-octylhexadecyl group, a n-heptadecyl group, a n-octadecyl group, a n-nonadecyl group, a n-icosyl group, a 2-ethylicosyl group, a 2-butylicosyl group, a 2-hexylicosyl group, a 2-octylicosyl group, a n-henicosyl group, a n-docosyl group, a n-tricosyl group, a n-tetracosyl group, a n-pentacosyl group, a n-hexacosyl group, a n-heptacosyl group, a n-octacosyl group, a n-nonacosyl group, a n-triacontyl group, etc.

At least one of $Ar^1$ and $Ar^2$ may be a substituted or unsubstituted aryl group having 6 to 24 ring carbon atoms. Examples of the aryl group include a phenyl group, a naphthyl group, an anthracenyl group, a phenanthryl group, a biphenyl group, a terphenyl group, a quaterphenyl group, a quinquephenyl group, a sexiphenyl group, a fluorenyl group, a triphenylene group, a biphenylene group, a pyrenyl group, a benzofluoranthenyl group, a chrysenyl group, etc.

In the above Formula (1), at least one of $Ar^1$ and $Ar^2$ may be a substituted or unsubstituted heteroaryl group having 4 to 30 ring carbon atoms (e.g., 5 to 35 ring atoms). Examples of the heteroaryl group include a benzothiazolyl group, a thiophenyl group, a thienothiophenyl group, a thienothienothiophenyl group, a benzothiophenyl group, a benzofuryl group, a dibenzothiophenyl group, a dibenzofuryl group, a N-arylcarbazolyl group, a N-heteroarylcarbazolyl group, a N-alkylcarbazolyl group, a phenoxazyl group, a phenothiazyl group, a pyridyl group, a pyrimidyl group, a triazinyl group, a quinolinyl group, a quinoxalyl group, etc. In an implementation, the dibenzothiophenyl group, the dibenzofuryl group, or the N-arylcarbazolyl group may be selected.

In the above Formula (1), L may be a single bond or a substituted or unsubstituted arylene group having 6 to 18 ring carbon atoms. The material for an organic EL device according to an example embodiment may include an amine compound combined at position 6 of an indolo[3,2,1-jk]carbazolyl group via a single bond or an aryl group having 6 to 18 ring carbon atoms as a connecting group, which may help realize high efficiency and long life of the organic EL device.

Examples of the aryl group having 6 to 18 ring carbon atoms that may be used as L in Formula (1) include a phenyl group, a naphthyl group, an anthracenyl group, a phenanthryl group, a biphenyl group, a terphenyl group, a fluorenyl group, a triphenylene group, a biphenylene group, a pyrenyl group, a chrysenyl group, etc.

The compound according to an example embodiment may have a molecular weight of, e.g., less than or equal to 1,000 when applied in a vacuum deposition process.

The material for an organic EL device according to an example embodiment uses an amine compound combined at position 6 of an indolo[3,2,1-jk]carbazolyl group with higher electron tolerance than that of a carbazolyl group as a hole transport material, and an organic EL device having high efficiency and long life may be manufactured.

The material for an organic EL device according to an example embodiment may include one or more compounds having the following structures.

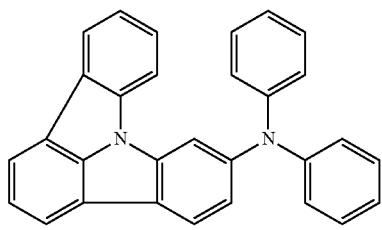

1

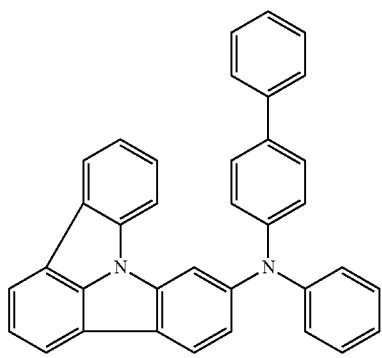

2

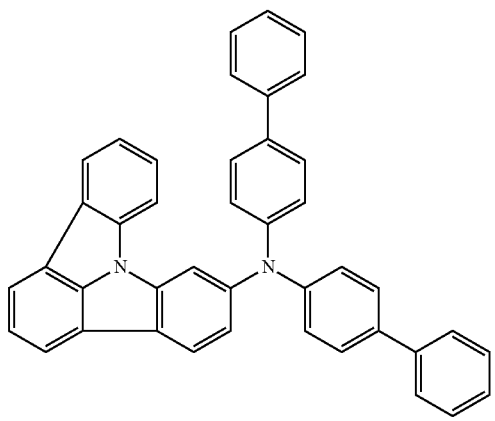

3

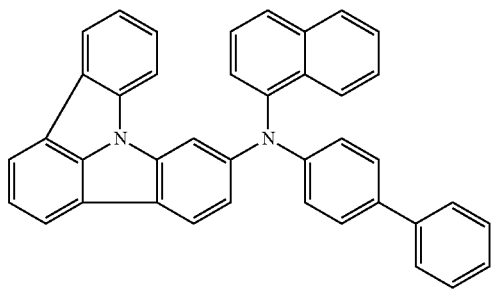

4

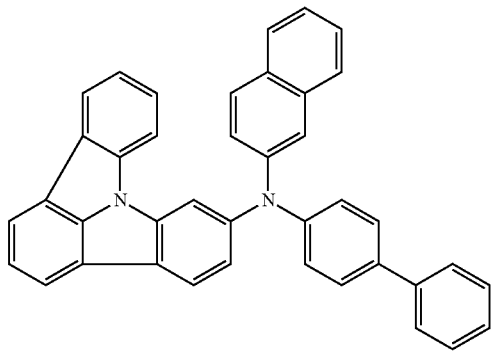

5

The material for an organic EL device according to an example embodiment may include one or more compounds having the following structures.
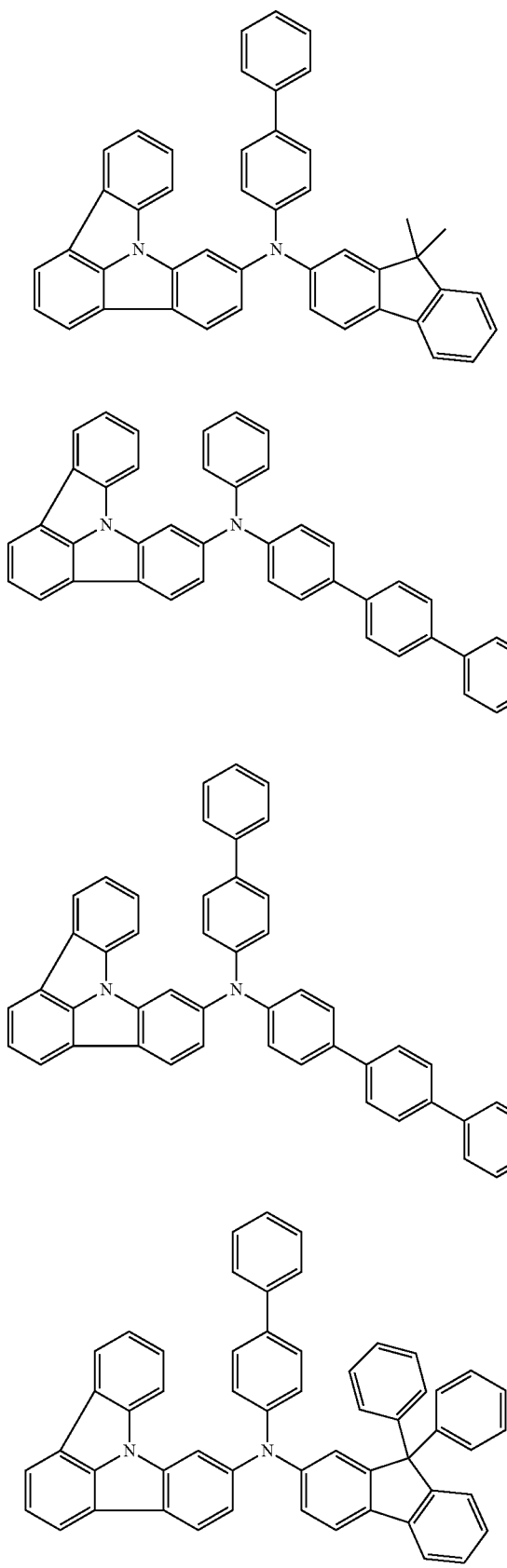

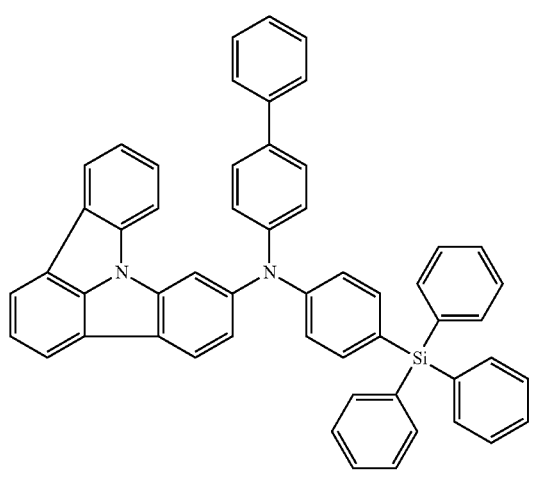
13
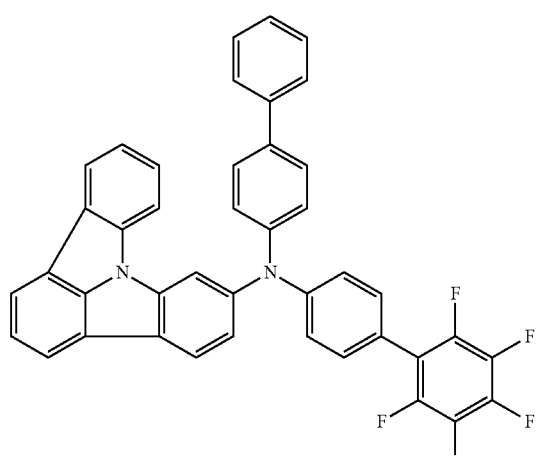
17
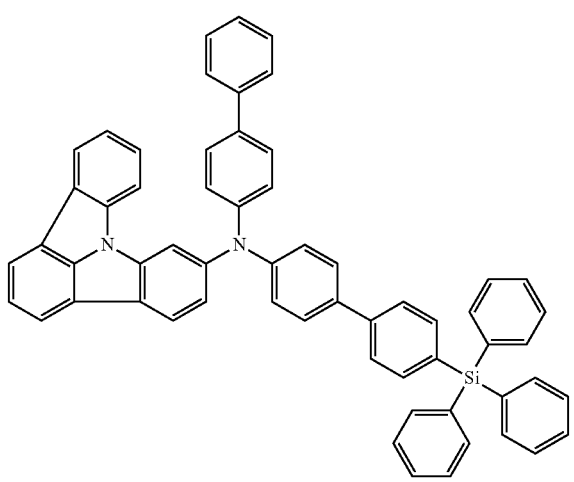
14
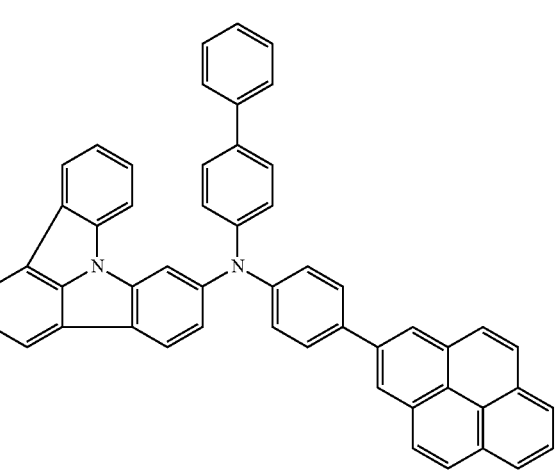
18
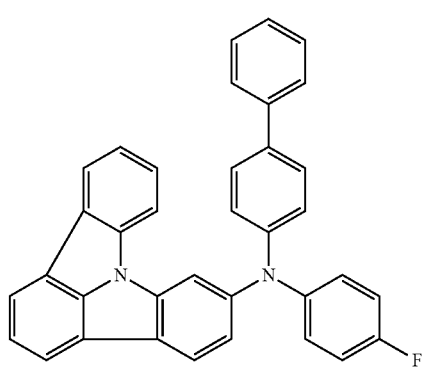
15
The material for an organic EL device according to an example embodiment may include one or more compounds having the following structures.
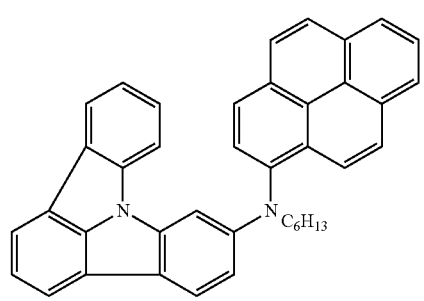
16
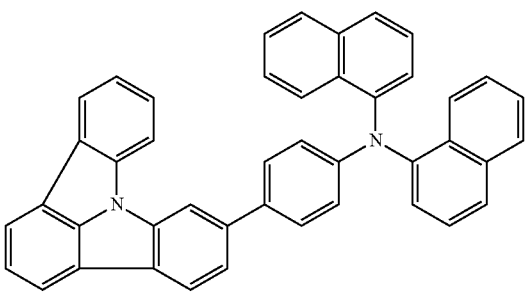
19

20
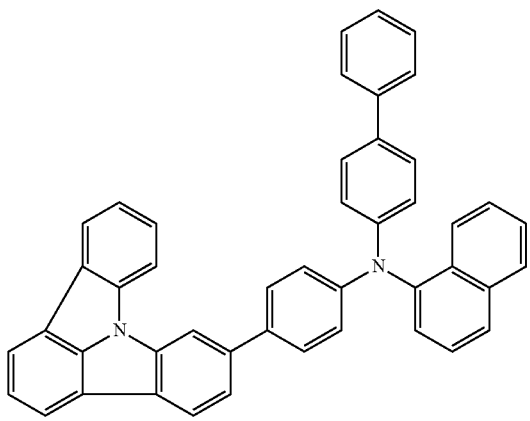
21
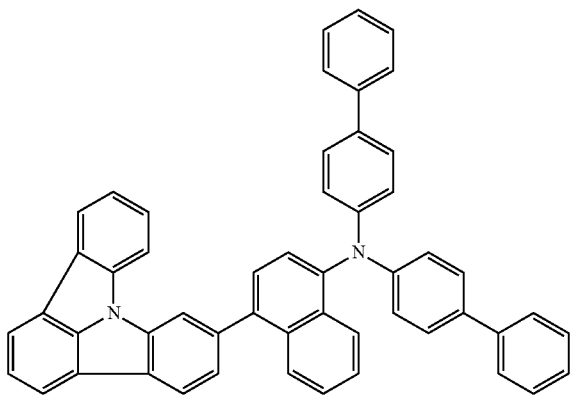
22
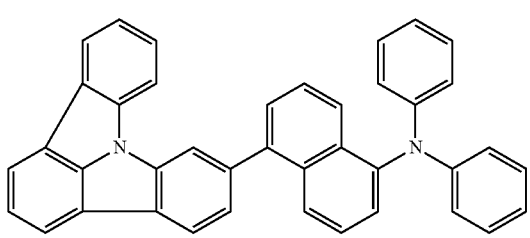
23
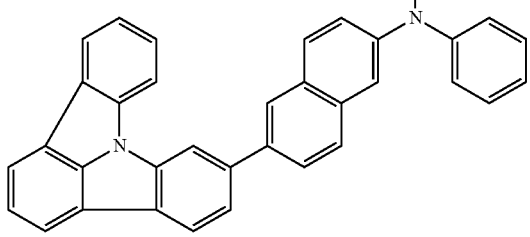
24
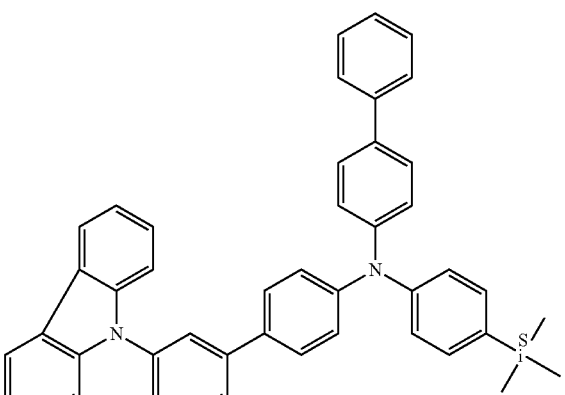
25
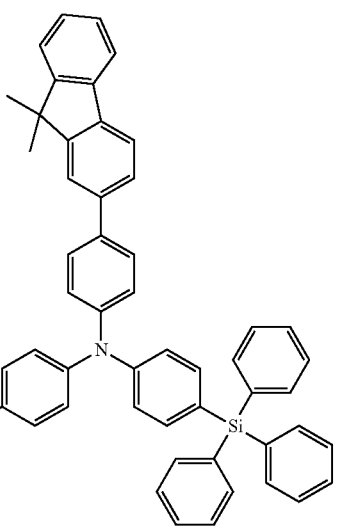
26
The material for an organic EL device according to an example embodiment may include one or more compounds having the following structures.

27
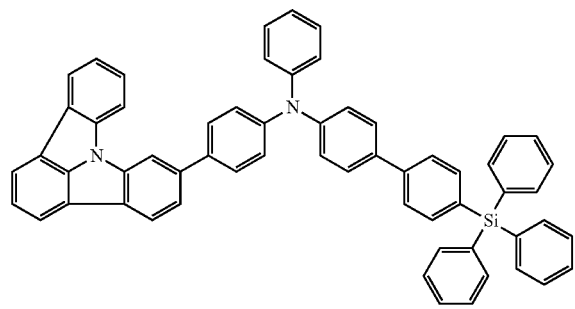
28
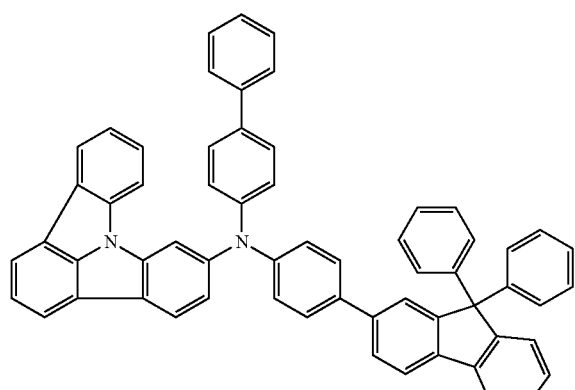
29
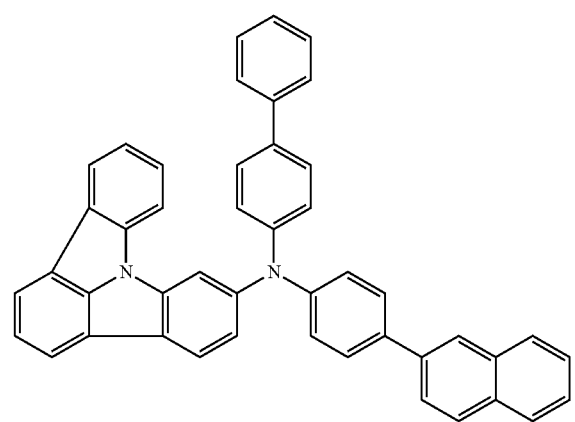
30
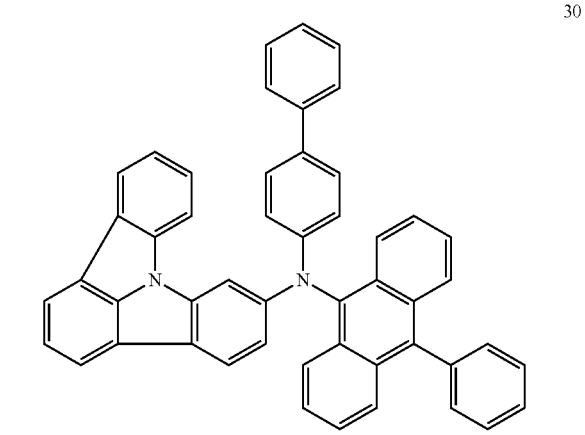
31
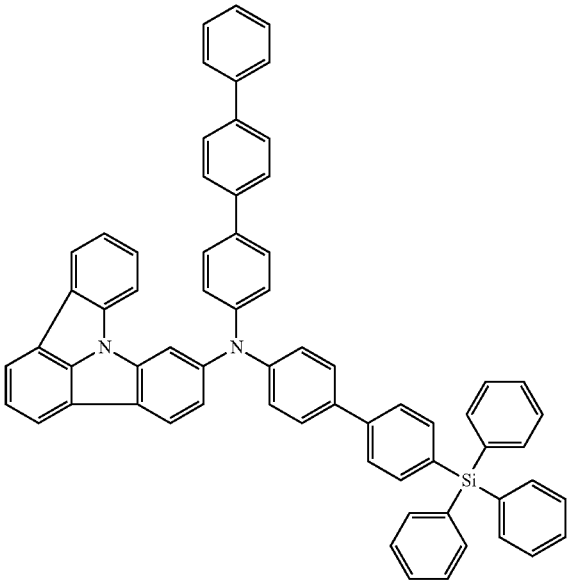
32
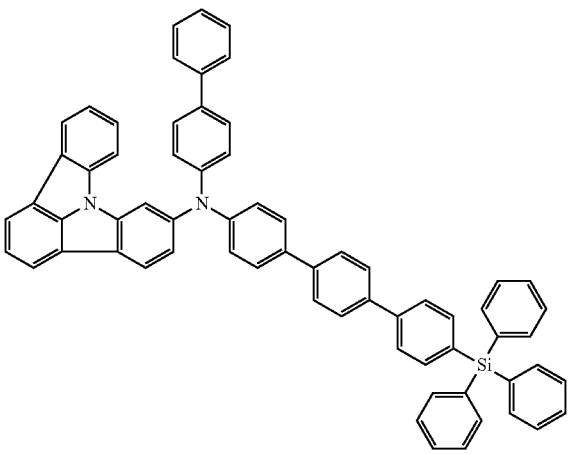
33
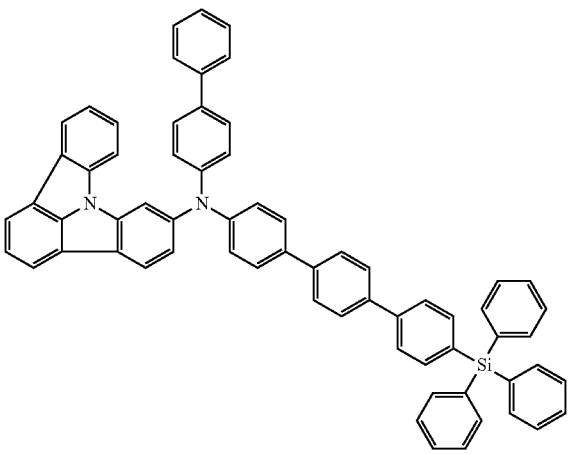
The material for an organic EL device according to an example embodiment may include one or more compounds having the following structures.

34
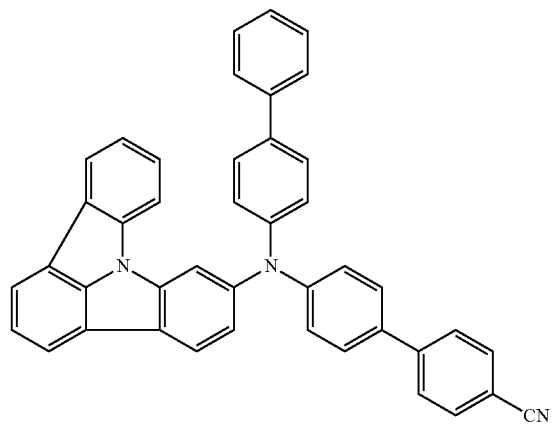
35
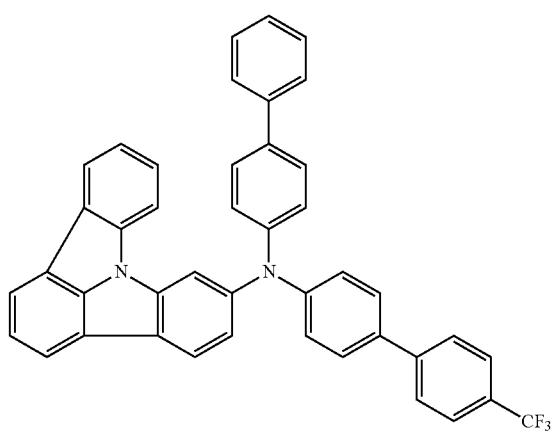
36
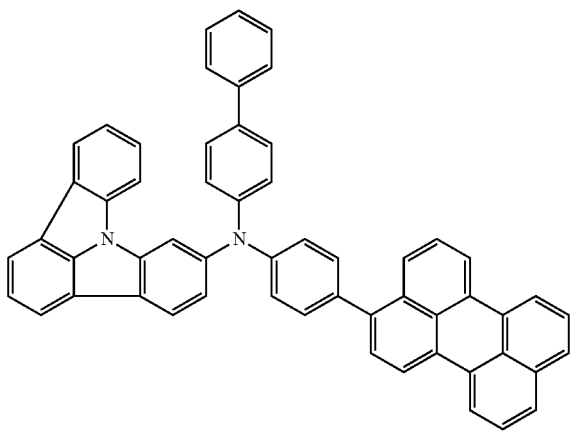
37
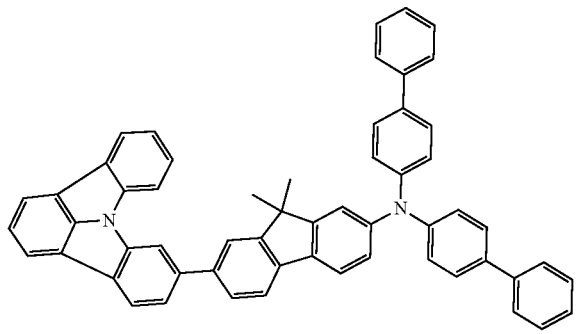
38
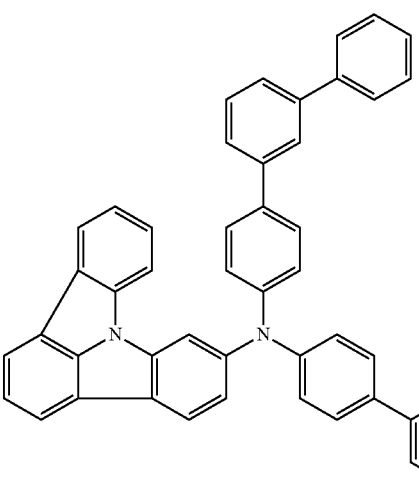
42
43
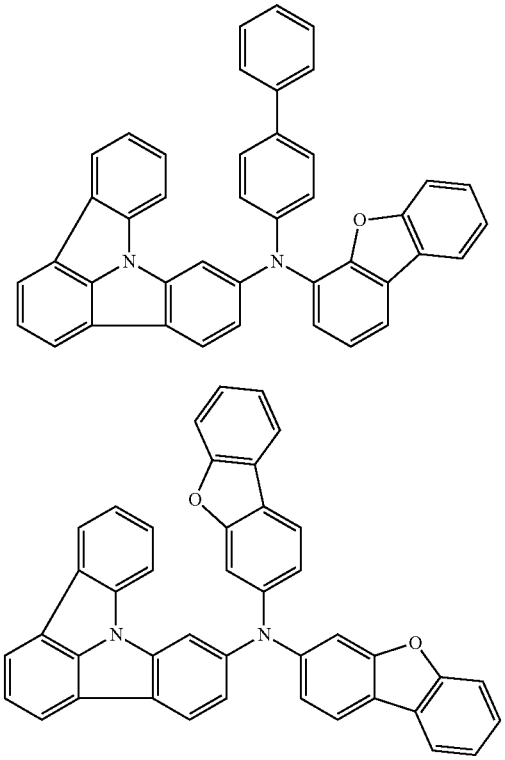

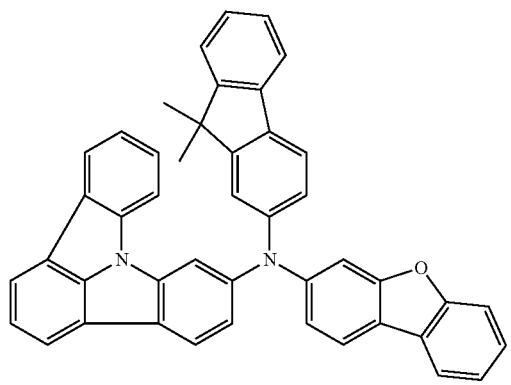
The material for an organic EL device according to an example embodiment may include one or more compounds having the following structures.
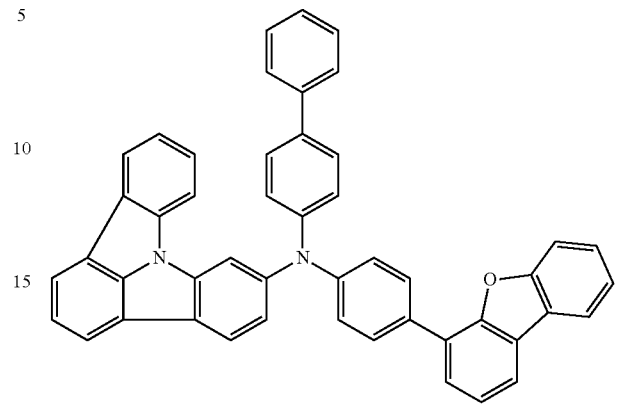
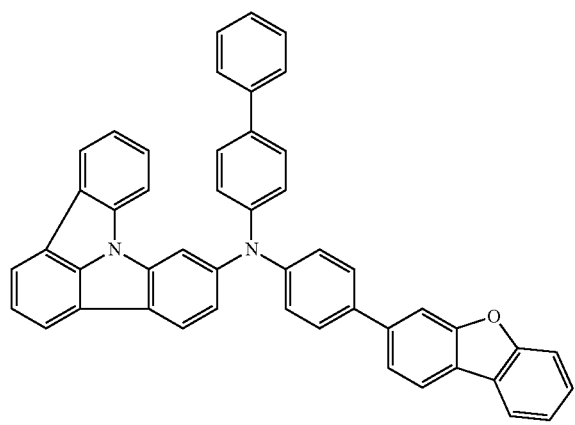
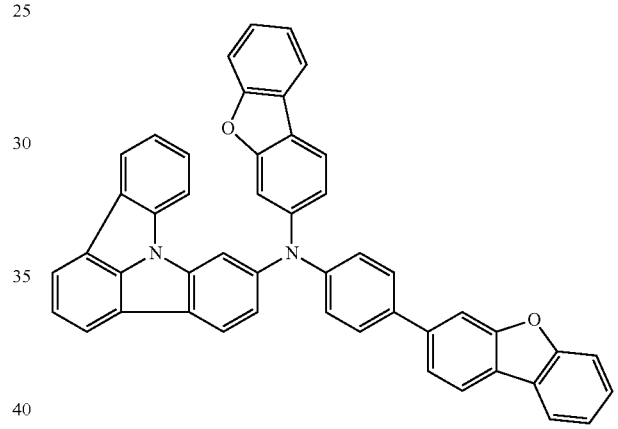
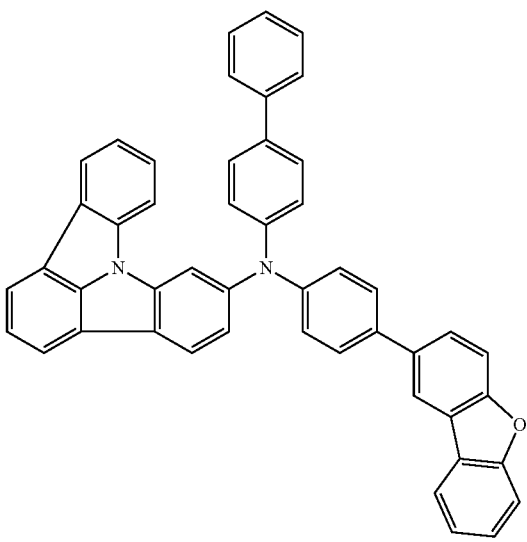
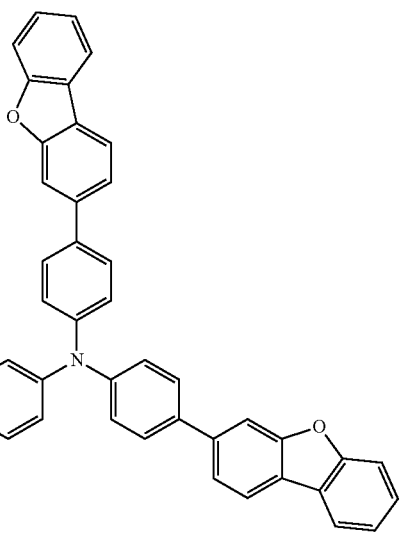

50
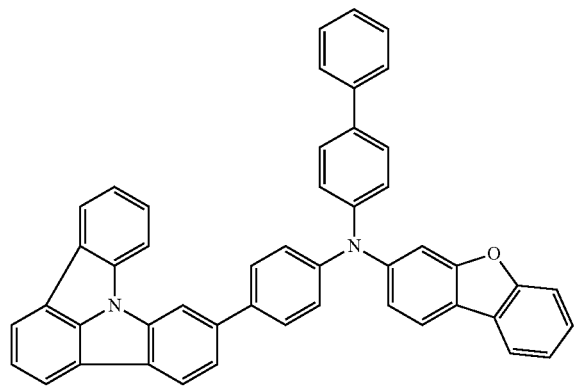
51
53
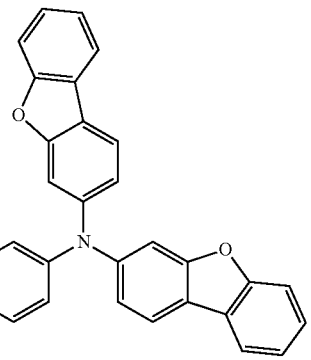
54
55
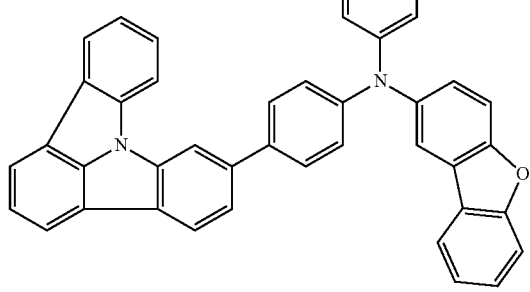
52
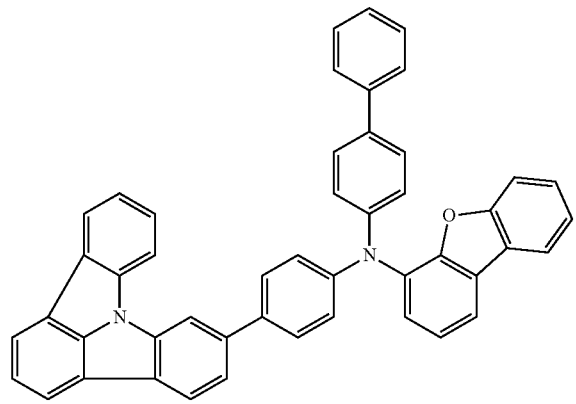
56
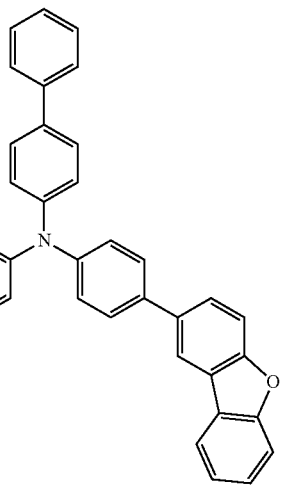
The material for an organic EL device according to an example embodiment may include one or more compounds having the following structures.

57
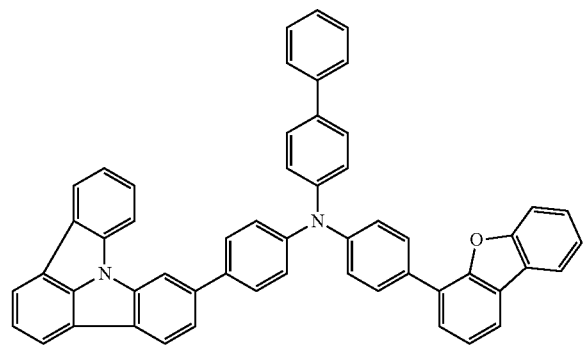
58
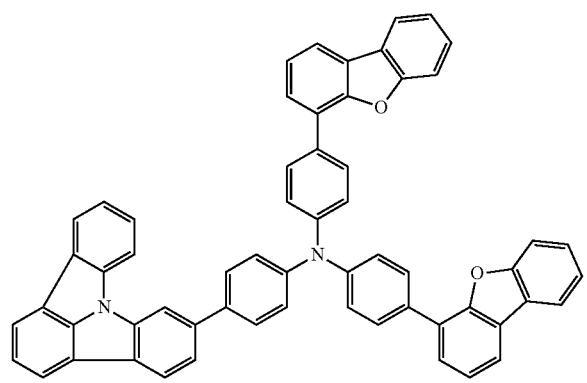
59
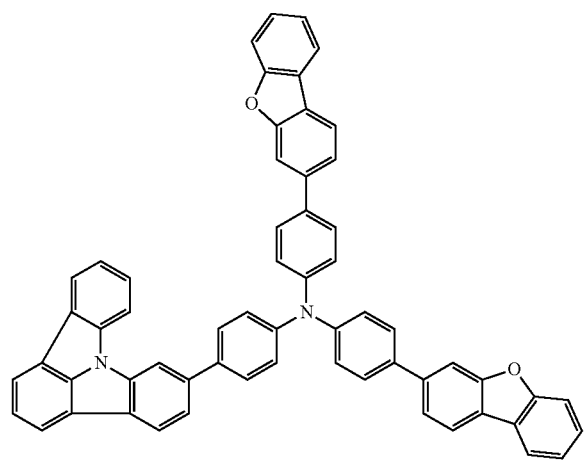
60
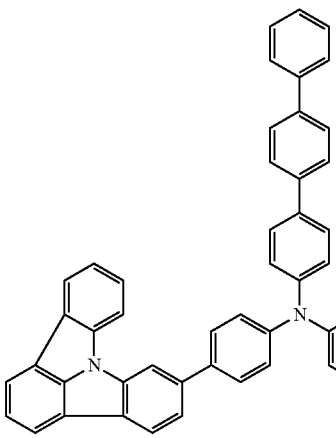
61
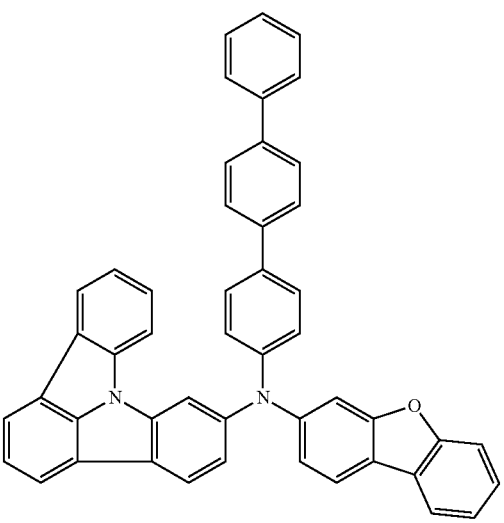
The material for an organic EL device according to an example embodiment may include one or more compounds having the following structures.
62
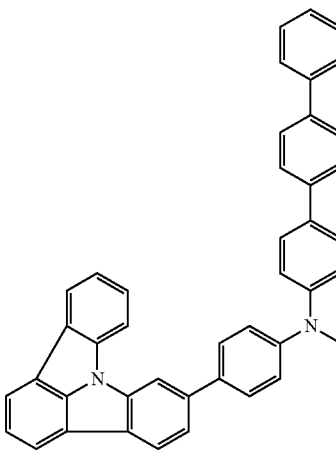

63
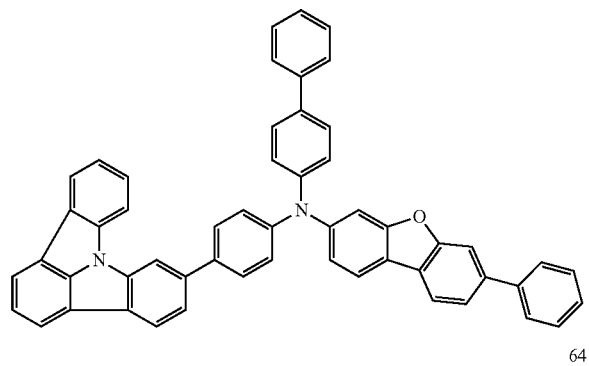
64
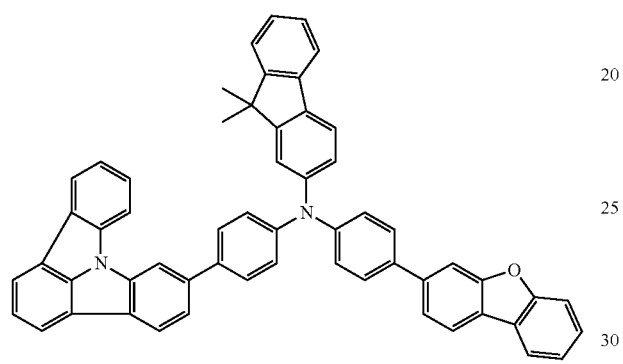
65
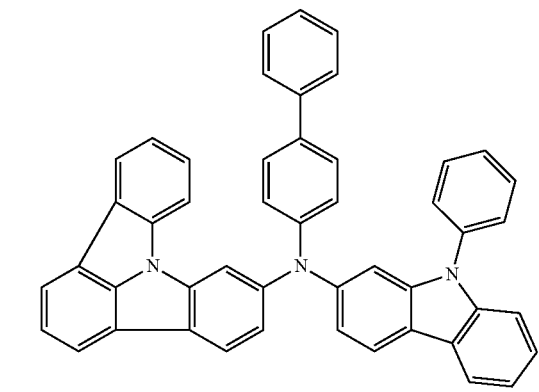
66
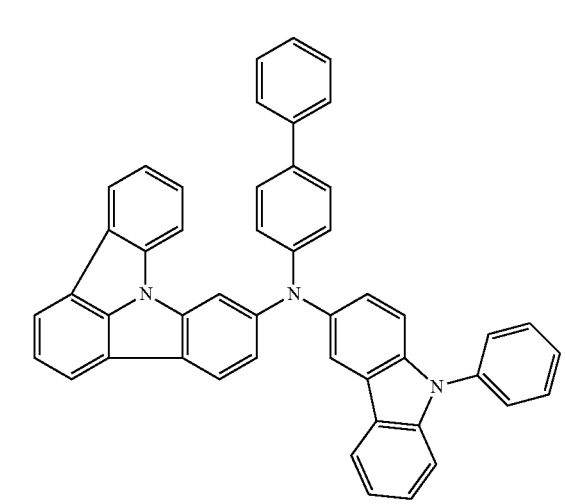
67
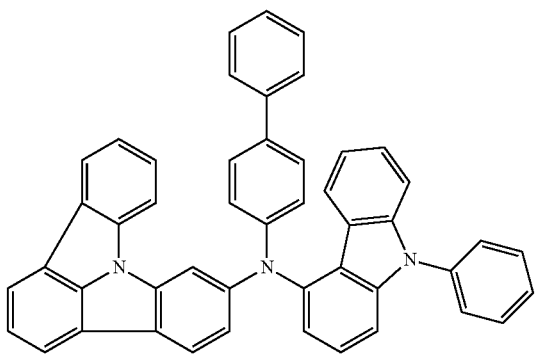
68
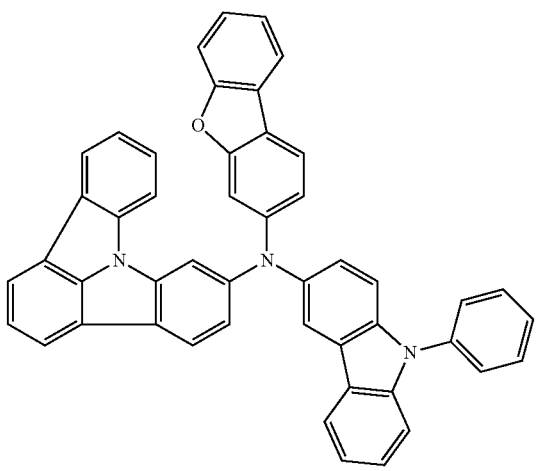
69
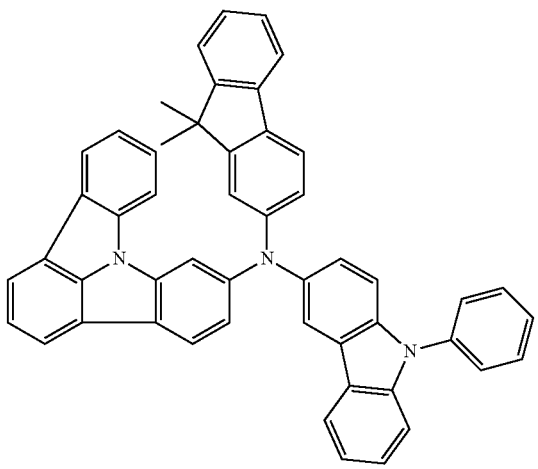
The material for an organic EL device according to an example embodiment may include one or more compounds having the following structures.

70
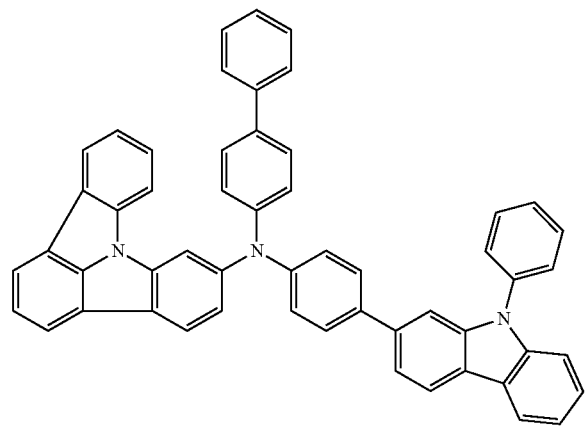
71
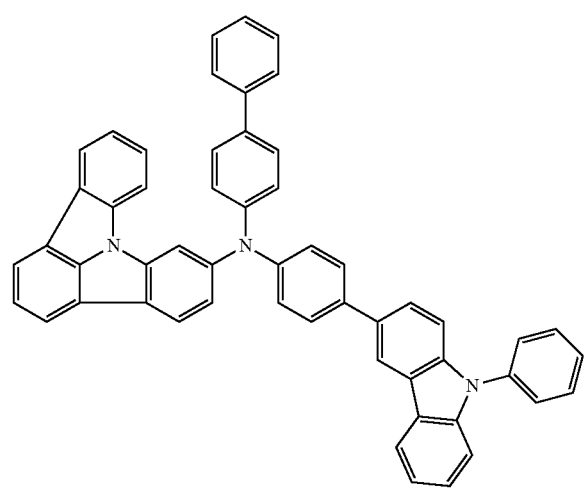
72
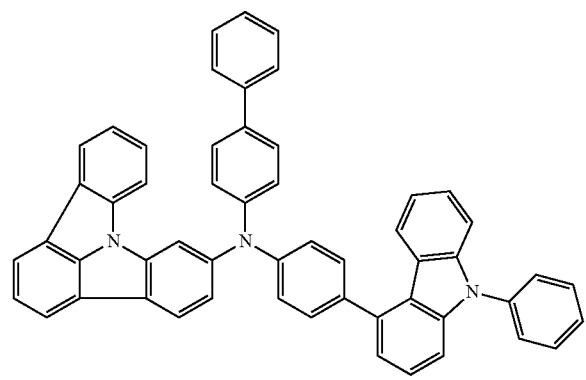
73
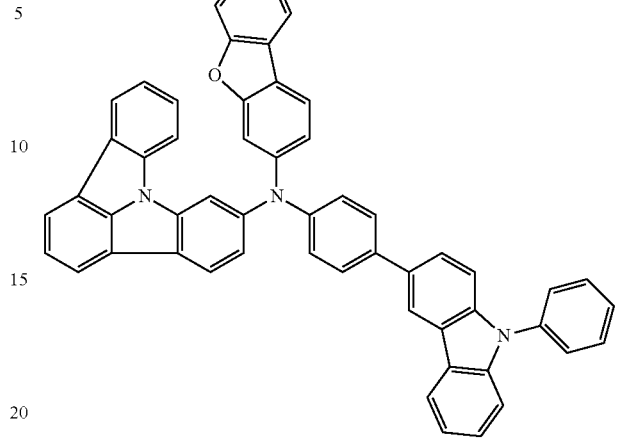
74
75
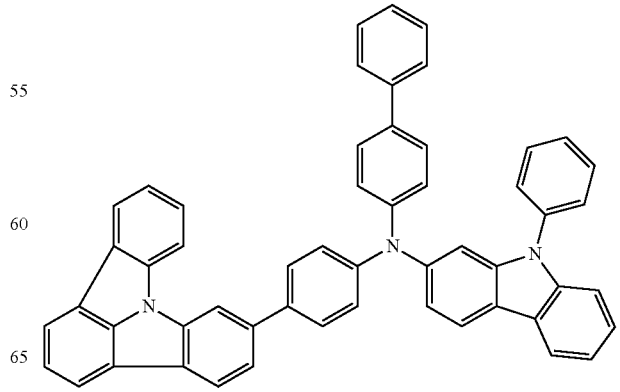

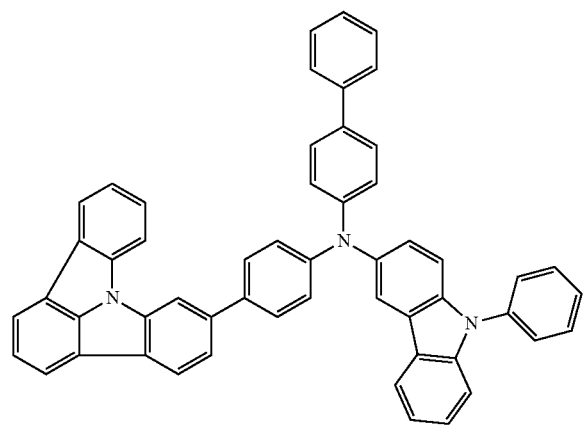
76
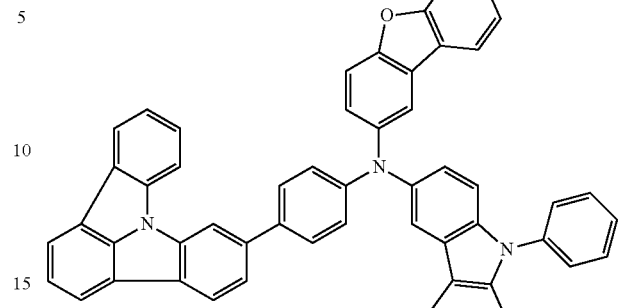
79
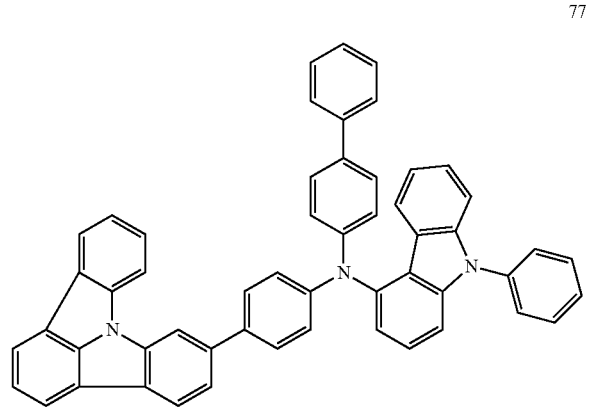
77
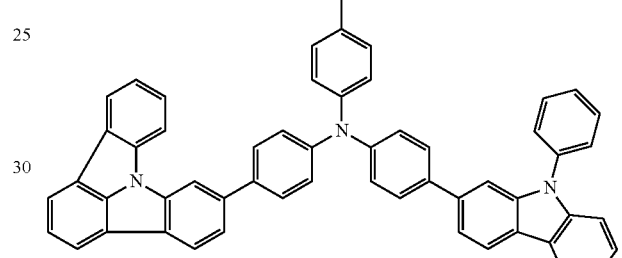
80
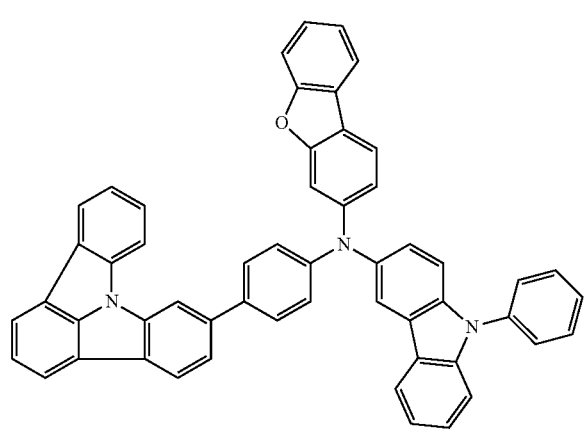
78
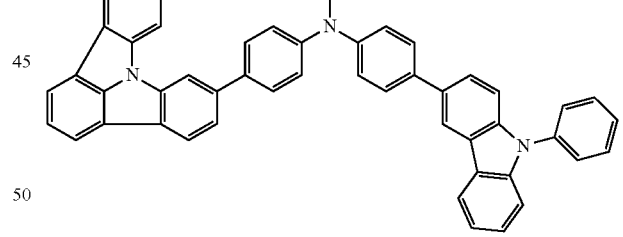
81
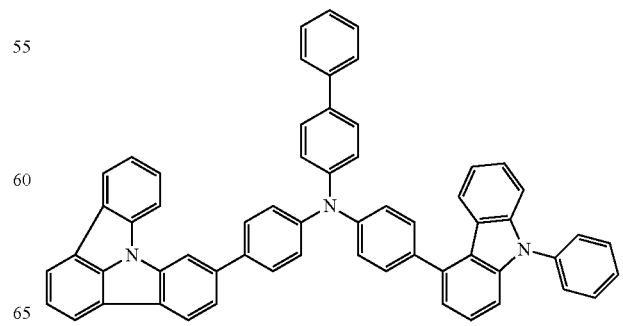
82
The material for an organic EL device according to an example embodiment may include one or more compounds having the following structures.

83
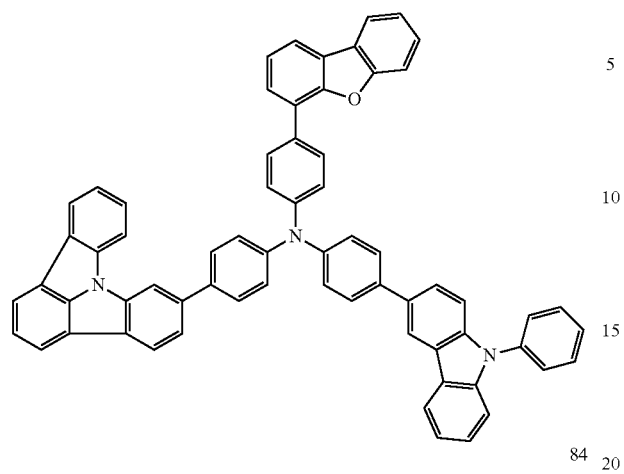
84
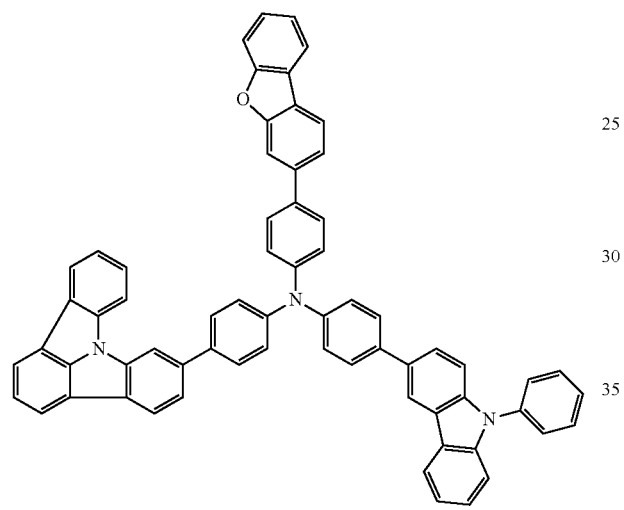
The material for an organic EL device according to an example embodiment may include one or more compounds having the following structures.
85
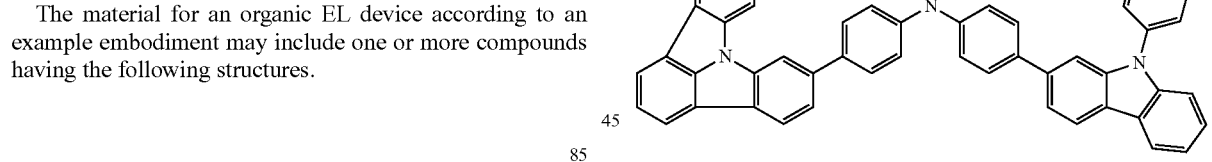
86
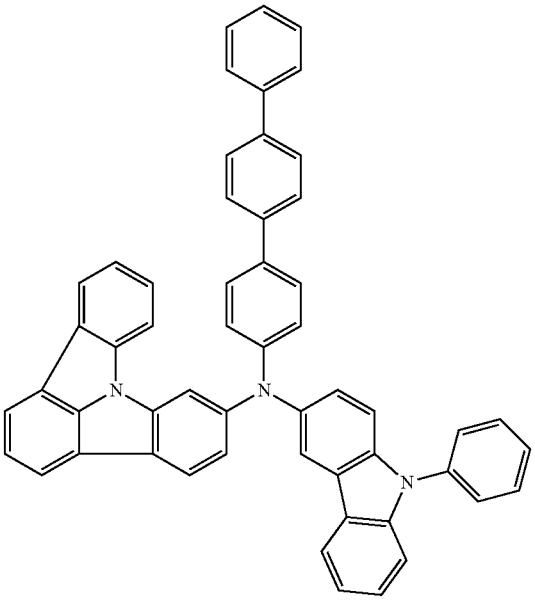
87
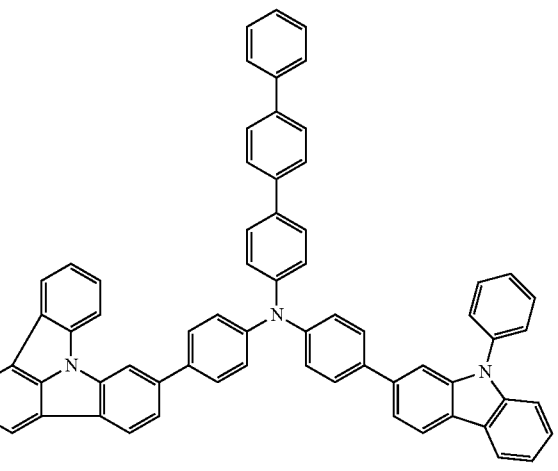
88
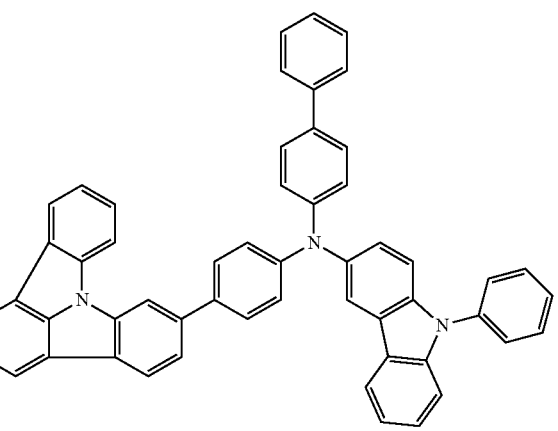

89
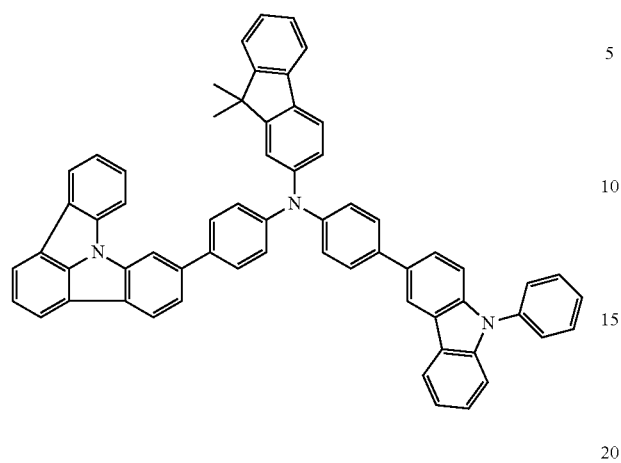
90
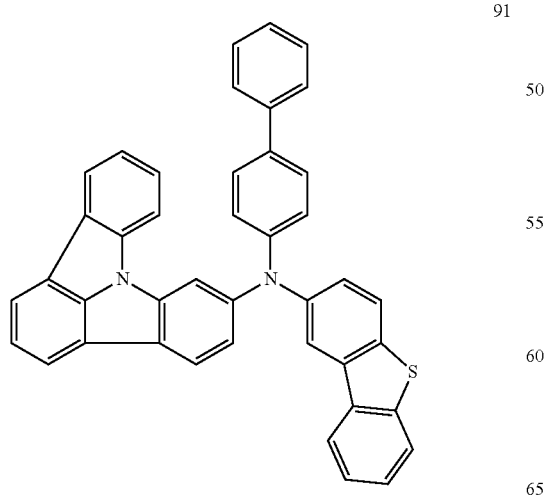
92
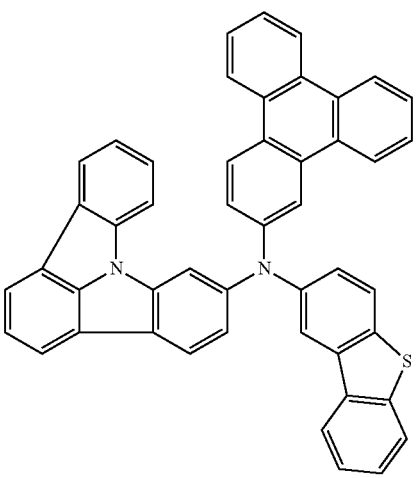
93
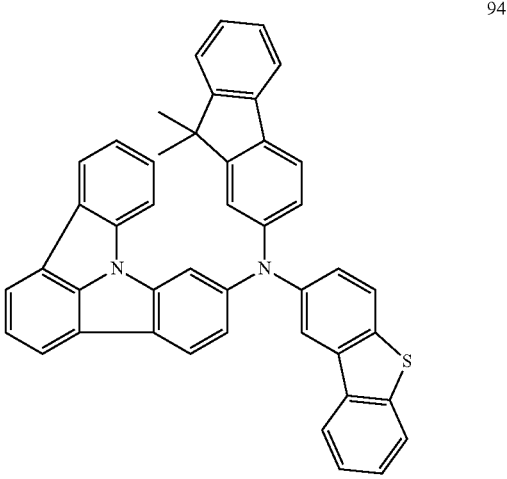
The material for an organic EL device according to an example embodiment may include one or more compounds having the following structures.
91
94

31
-continued
95
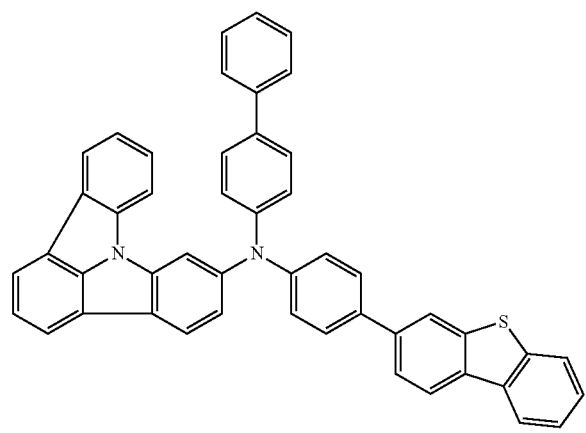
96
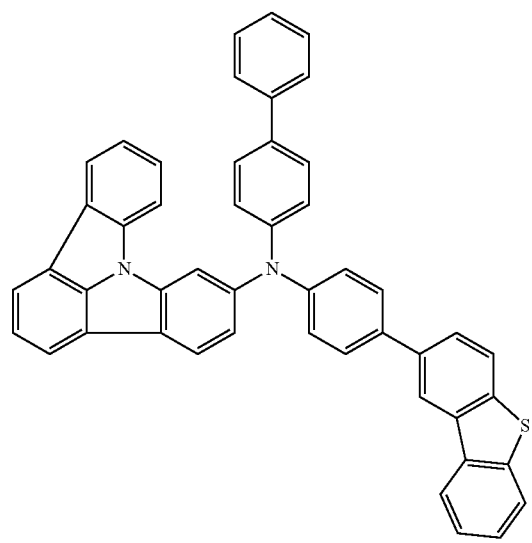
97
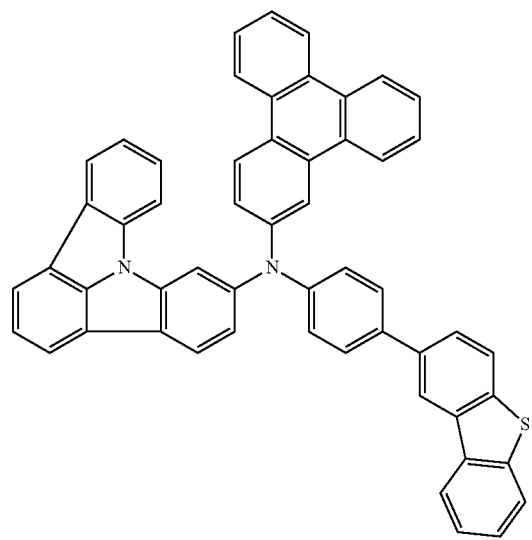
32
-continued
98
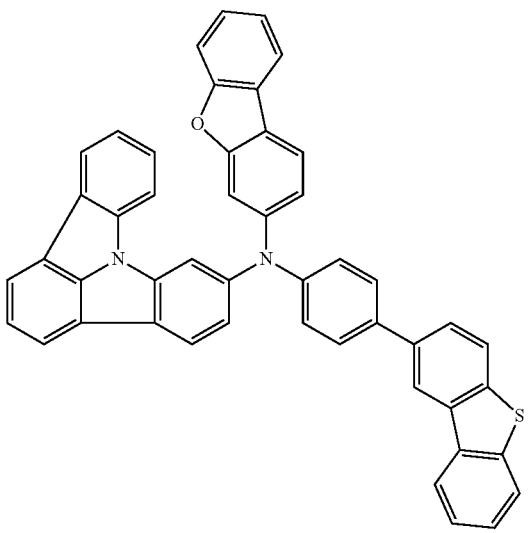
99
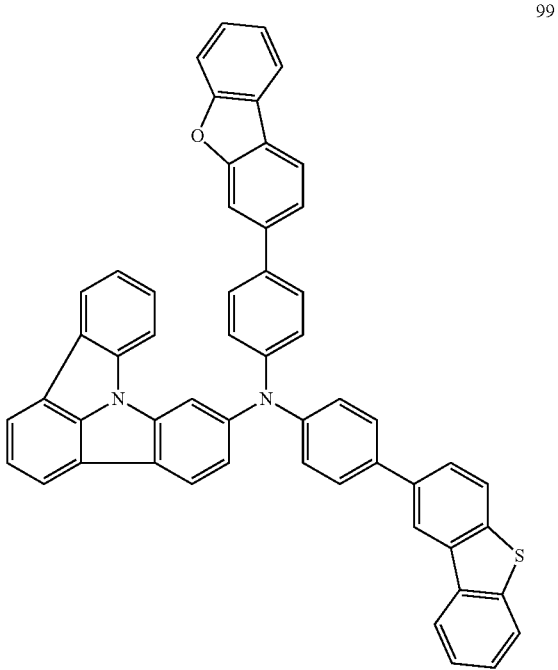
100

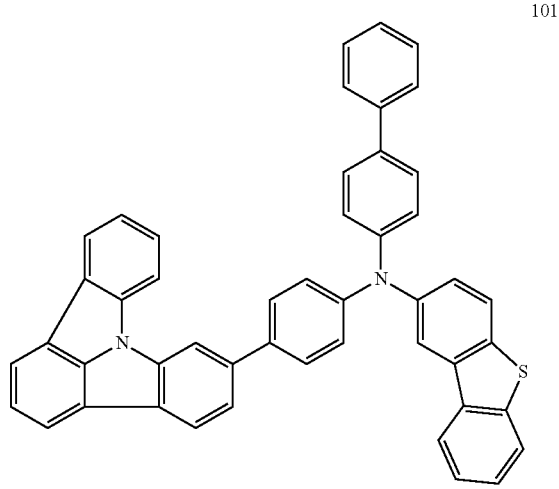
101
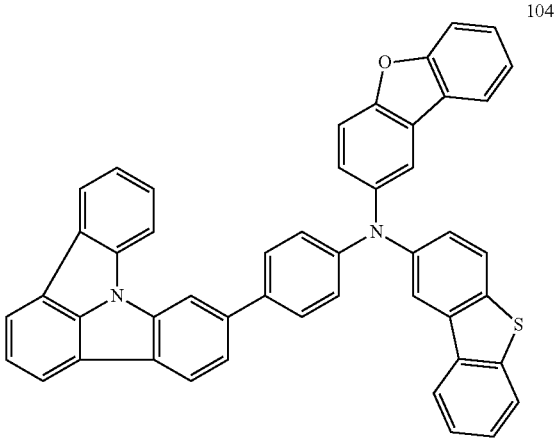
104
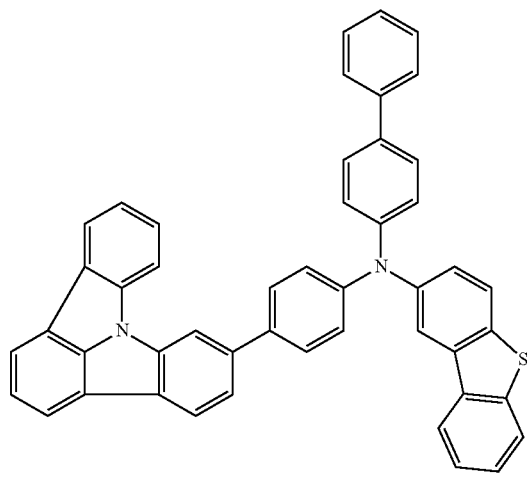
102
105
The material for an organic EL device according to an example embodiment may include one or more compounds having the following structures.
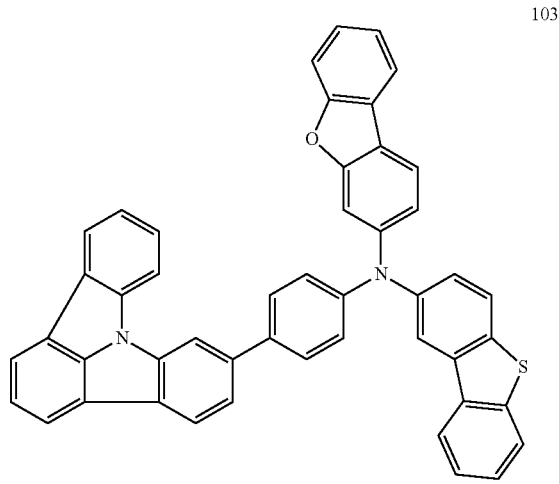
103
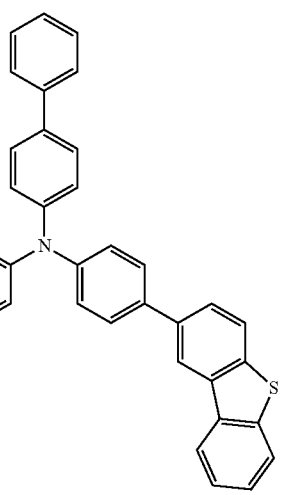
106

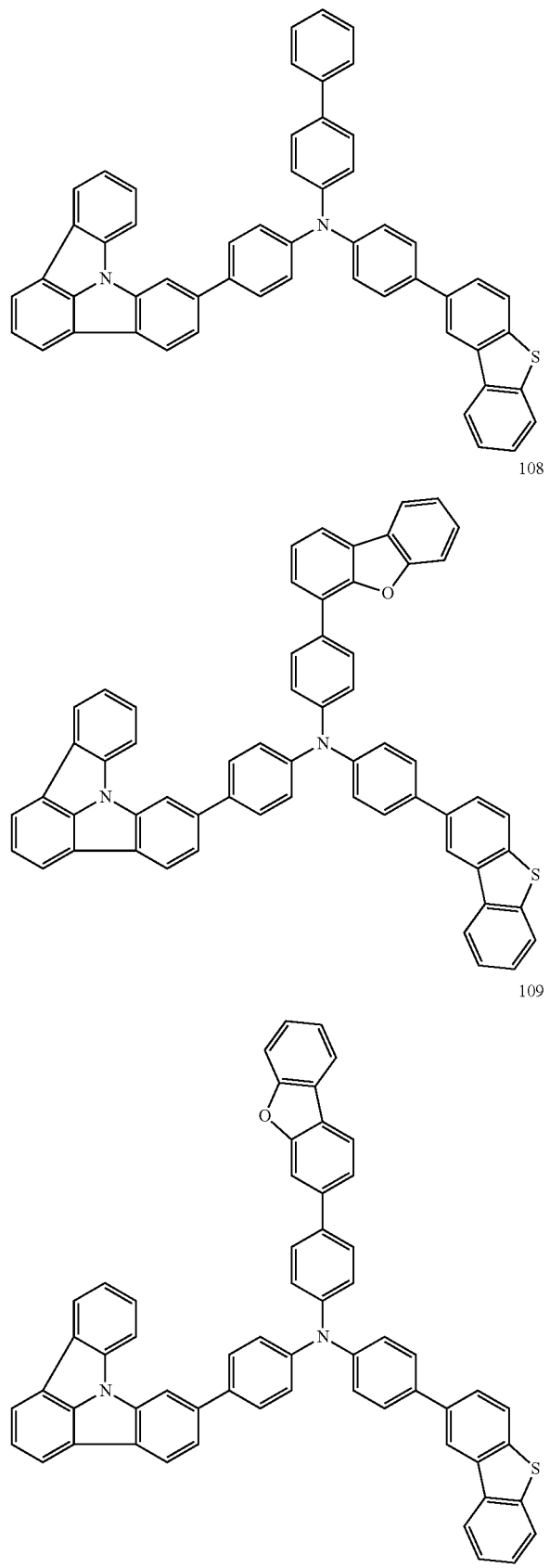
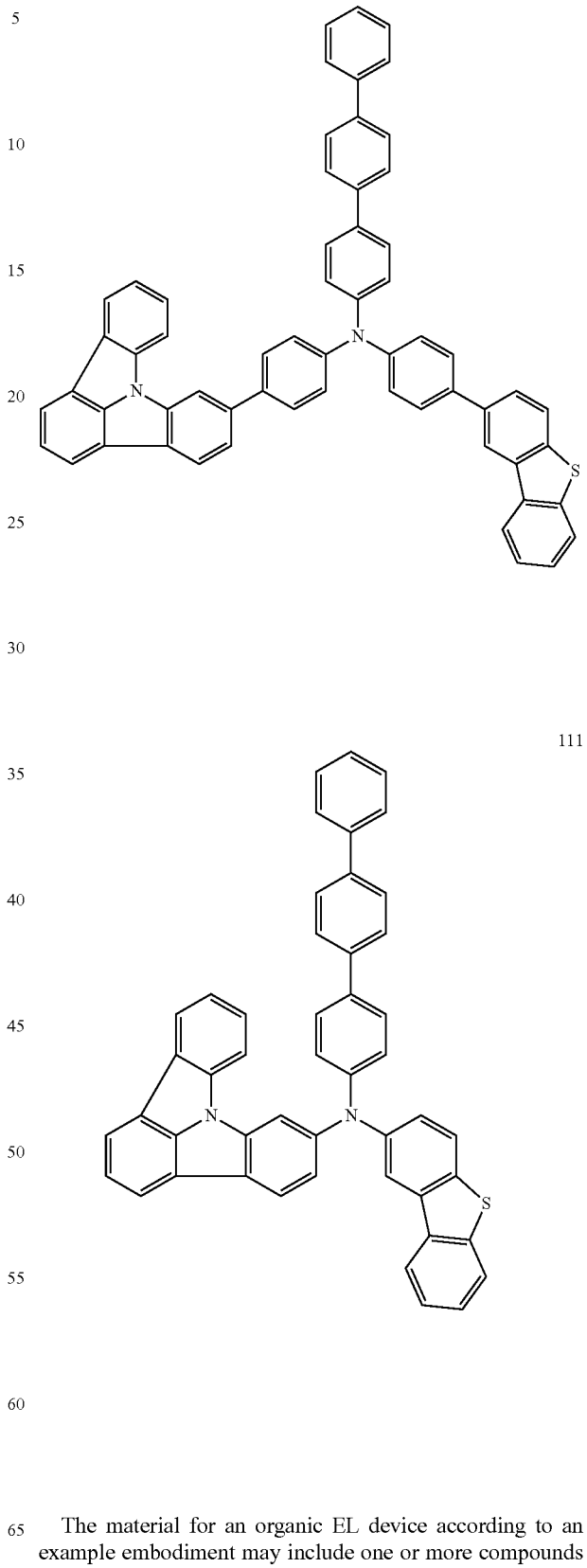
The material for an organic EL device according to an example embodiment may include one or more compounds having the following structures.

112
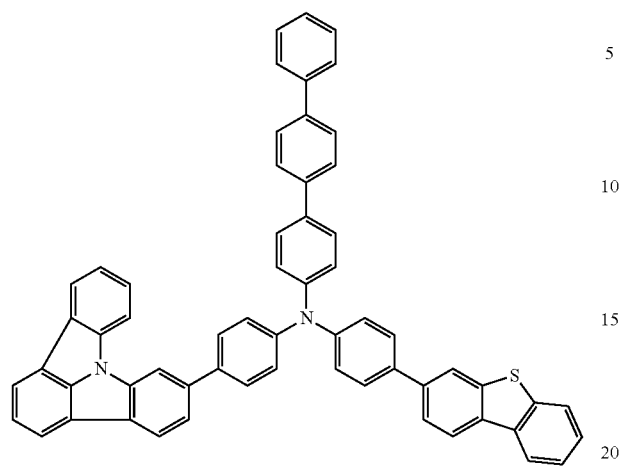
115
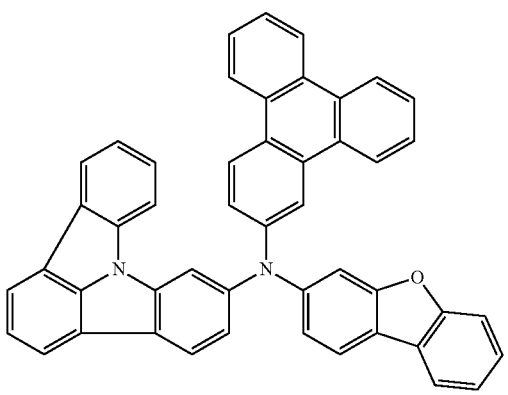
113
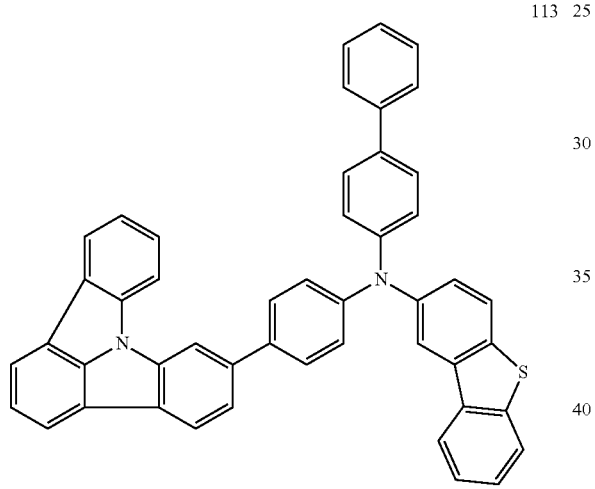
116
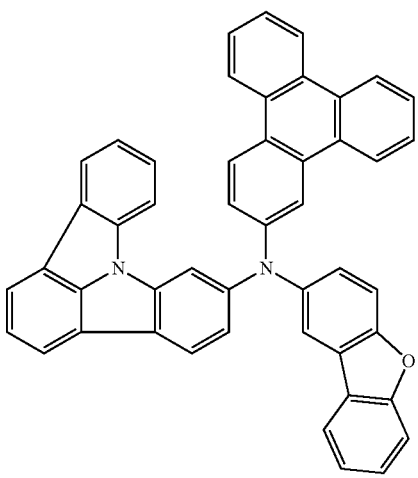
114
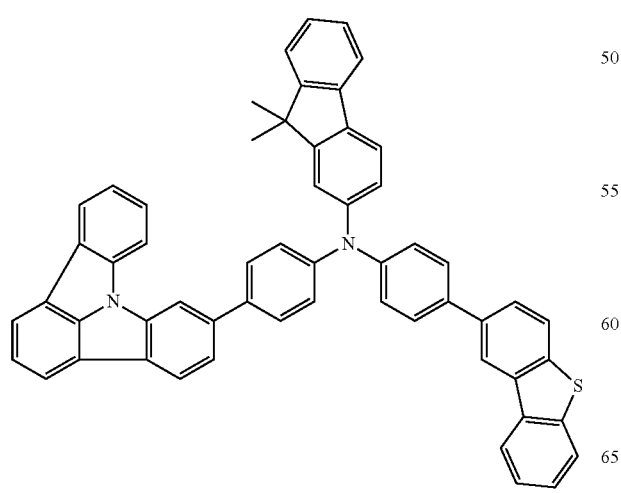
117
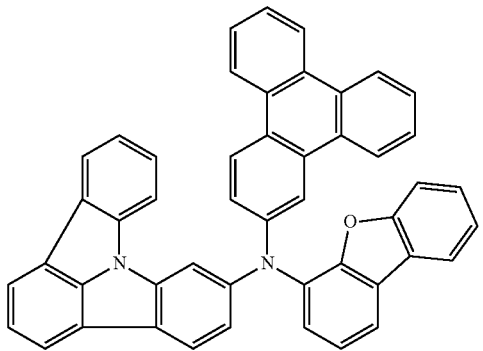

118
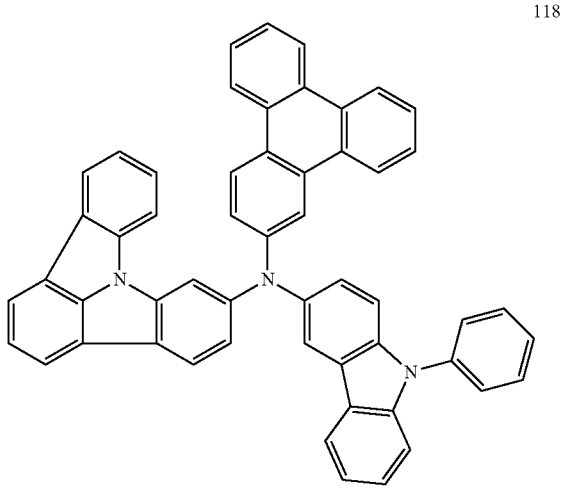
119
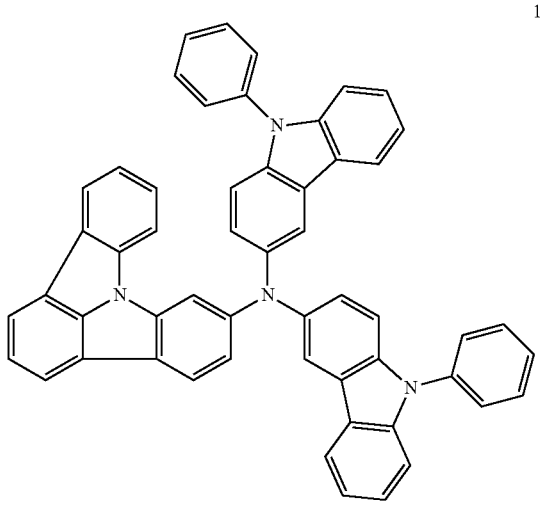
120
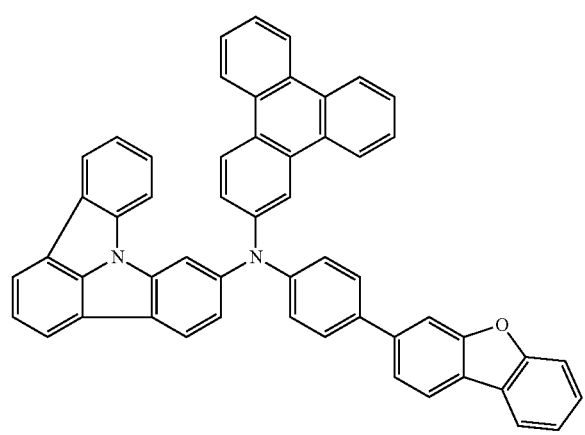
121
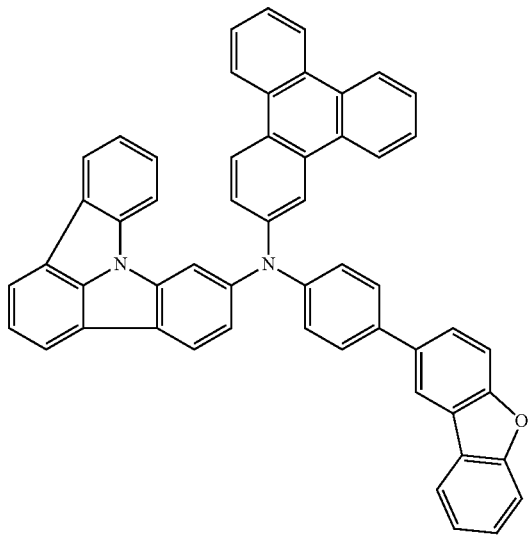
122
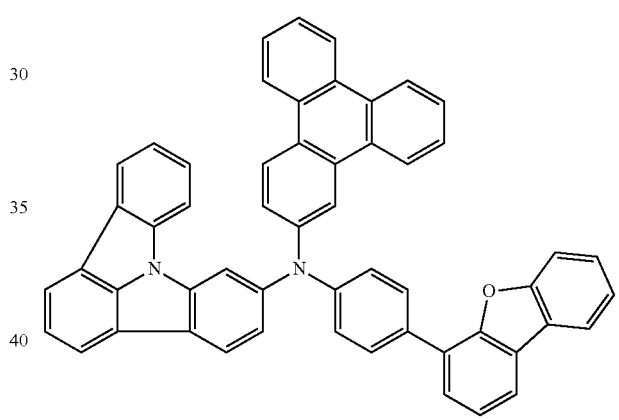
123
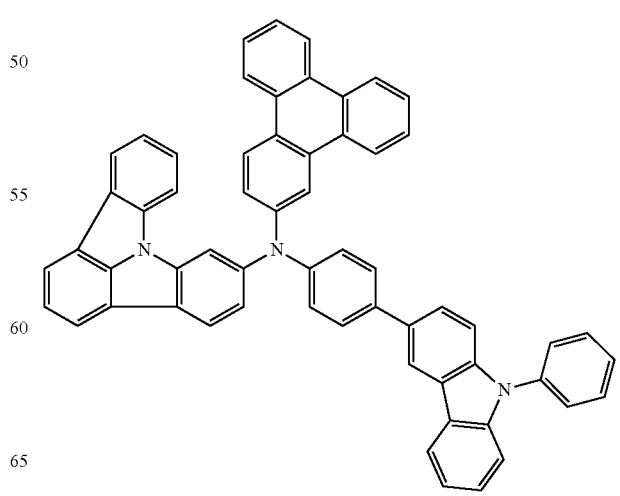
The material for an organic EL device according to an example embodiment may include one or more compounds having the following structures.

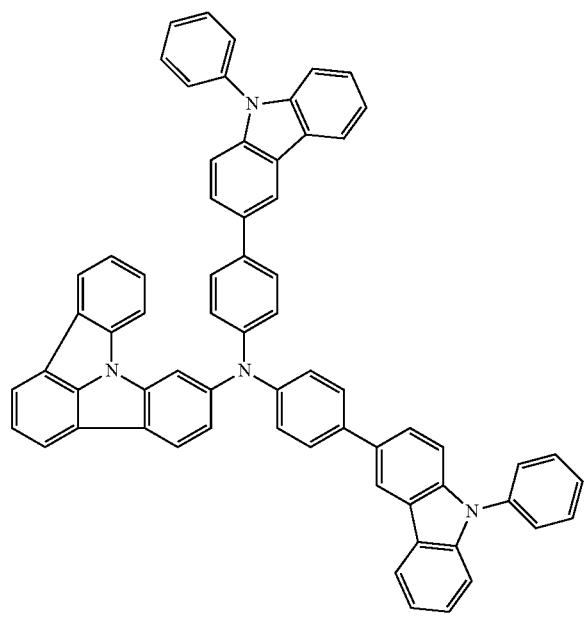
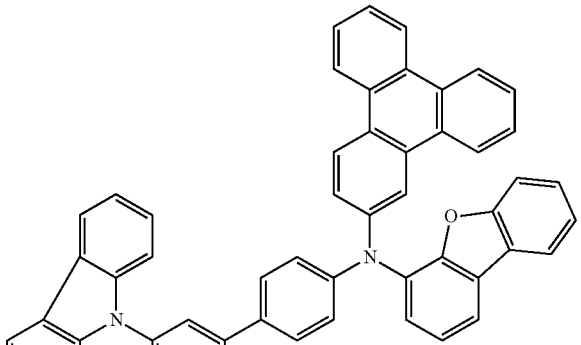
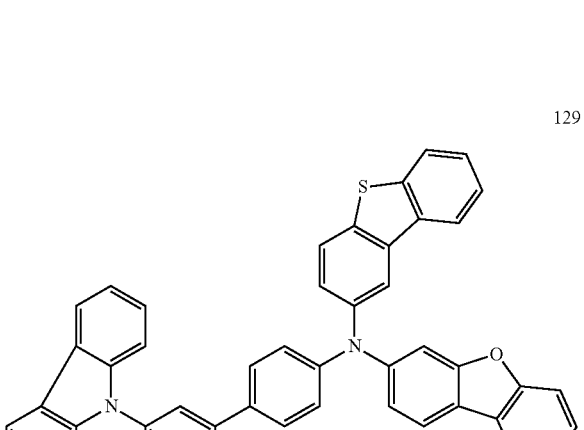
The material for an organic EL device according to an example embodiment may include one or more compounds having the following structures.

130
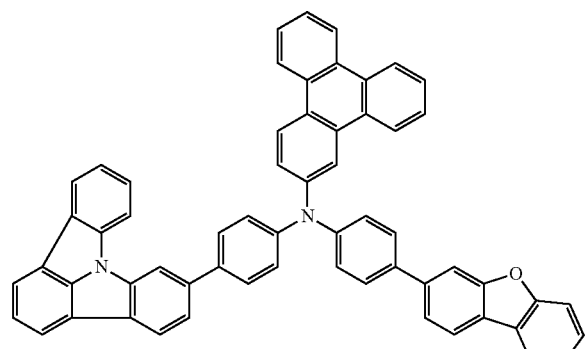
131
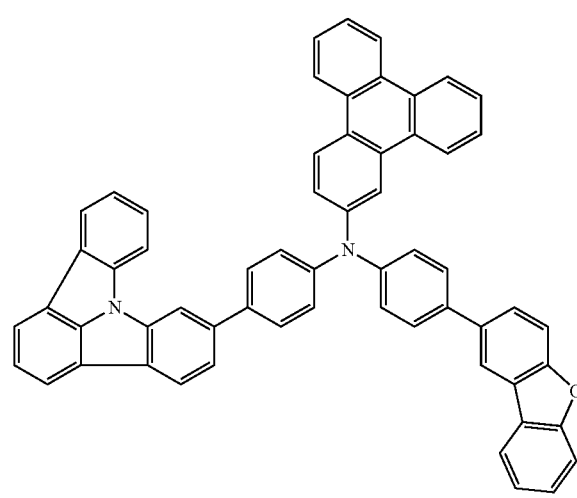
132
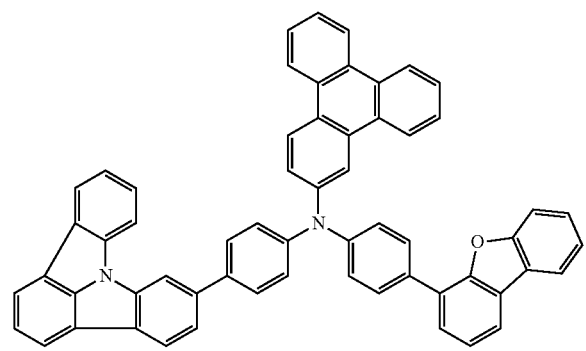
133
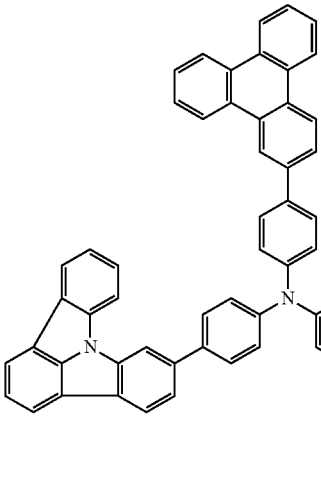
134
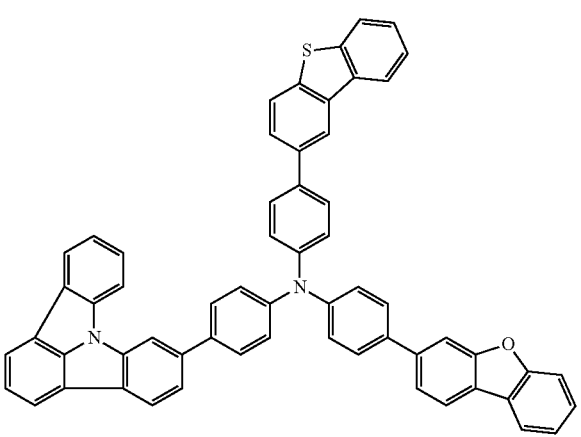
135
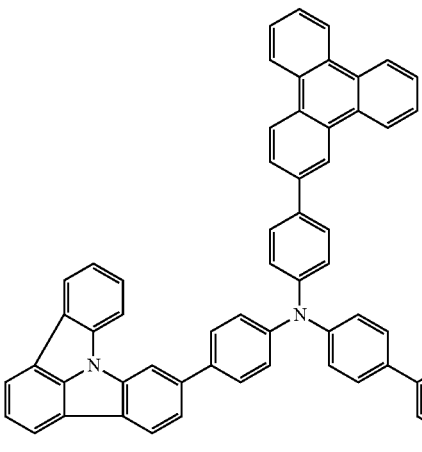
The material for an organic EL device according to an example embodiment may include one or more compounds having the following structures.

136
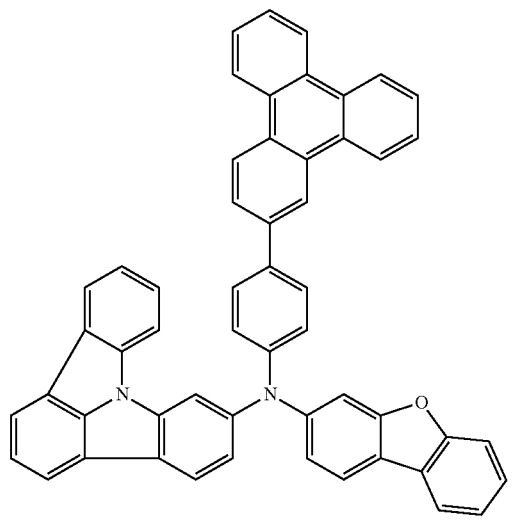
137
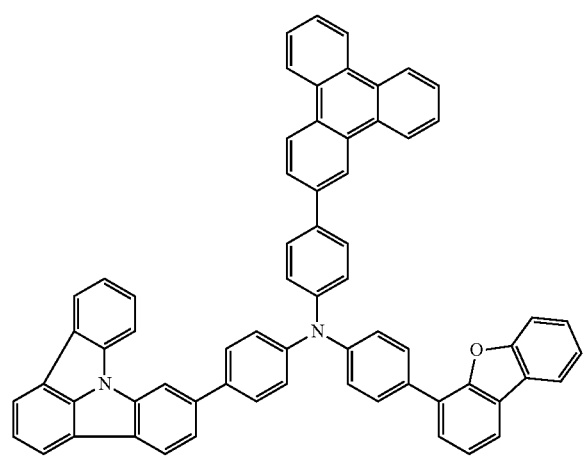
138
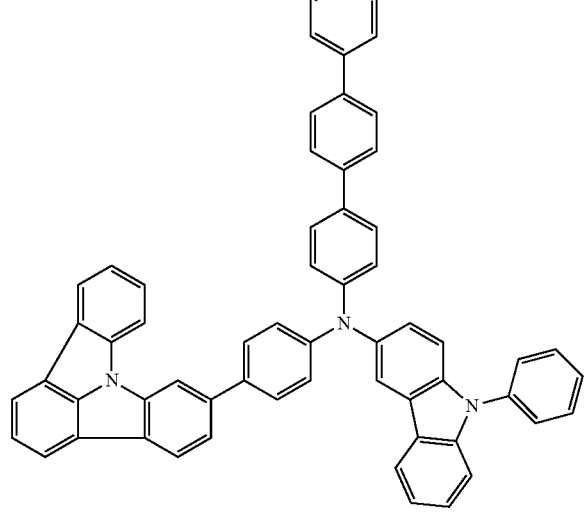
139
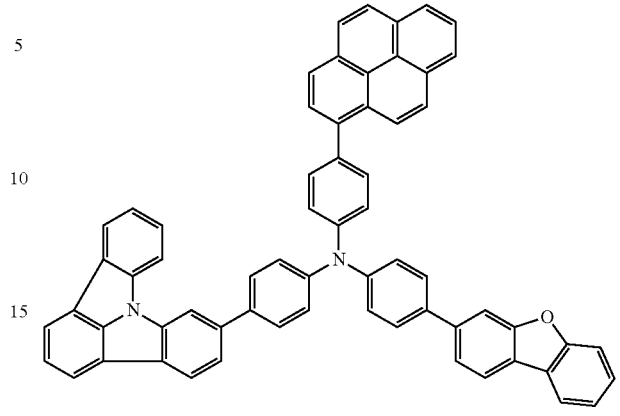
140
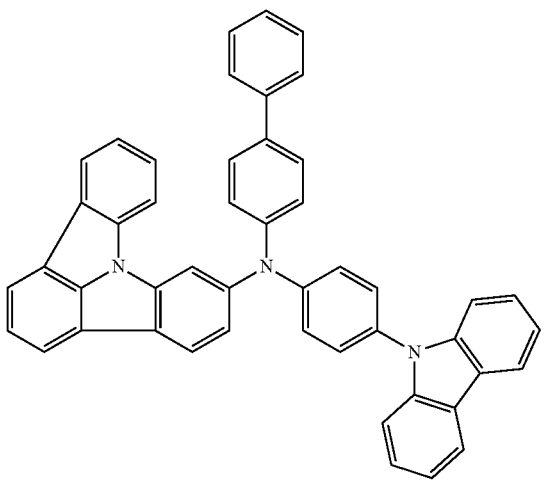
141
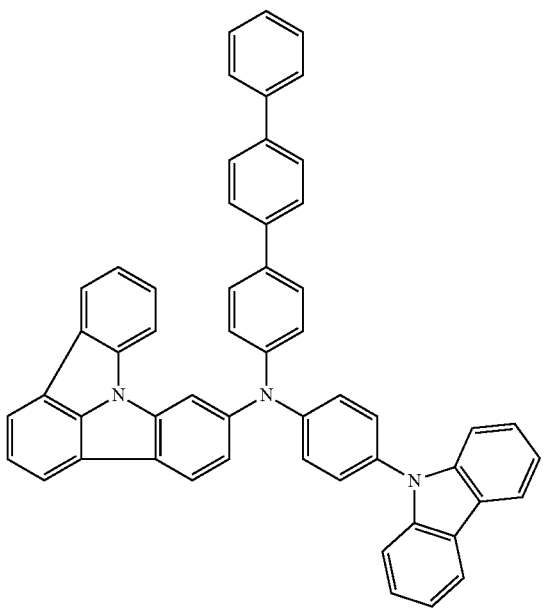

142
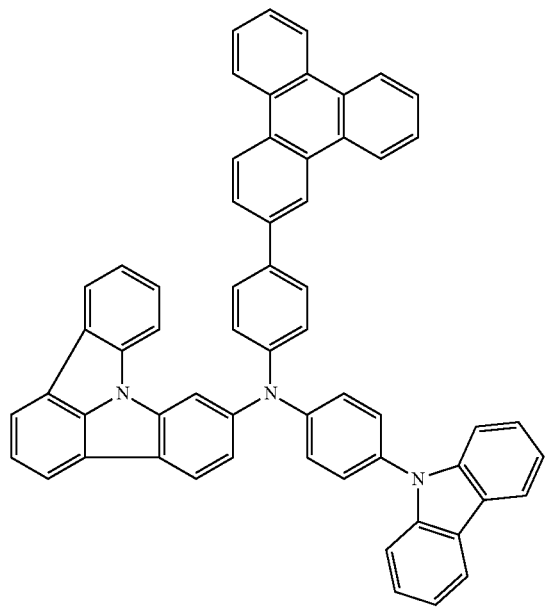
144
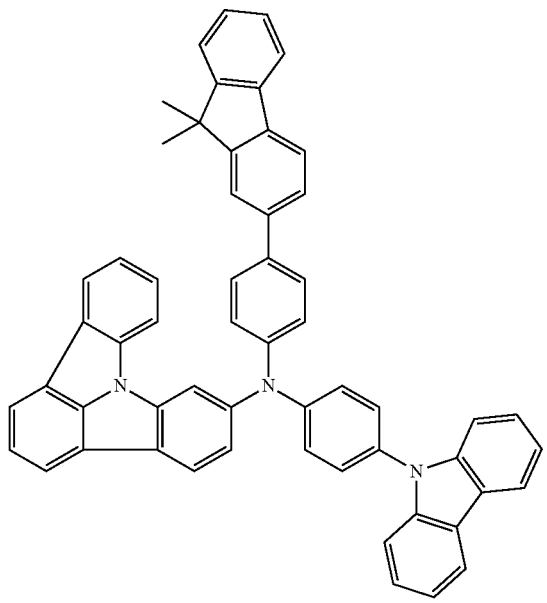
The material for an organic EL device according to an example embodiment may include one or more compounds having the following structures.
143
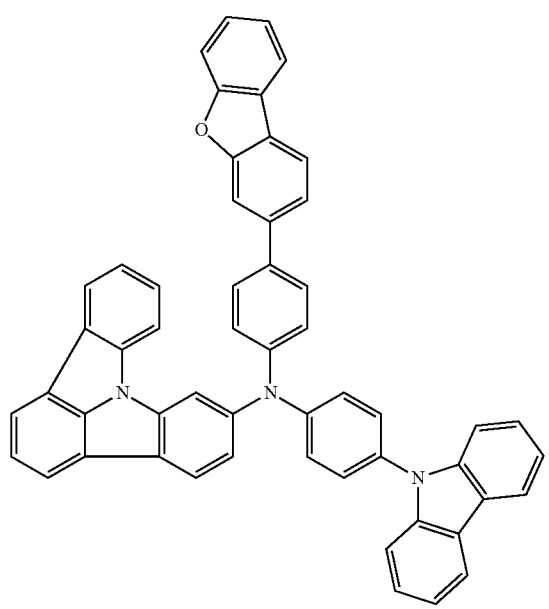
145
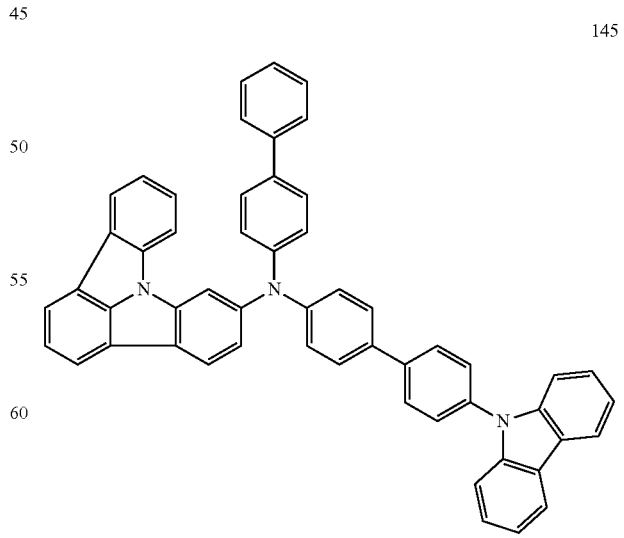

146
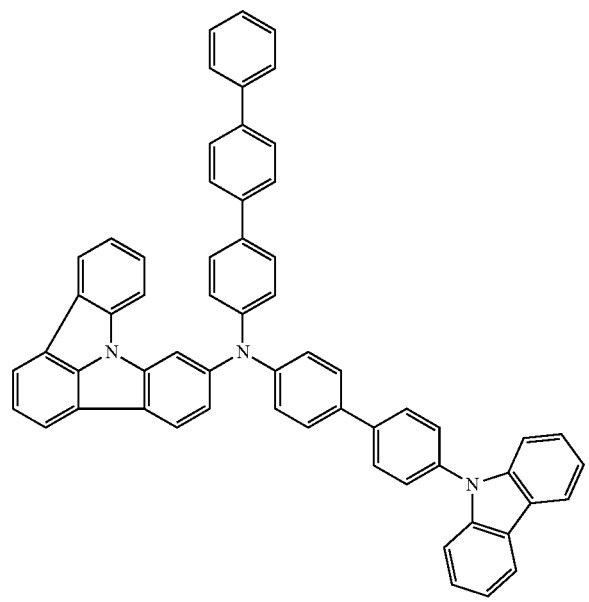
147
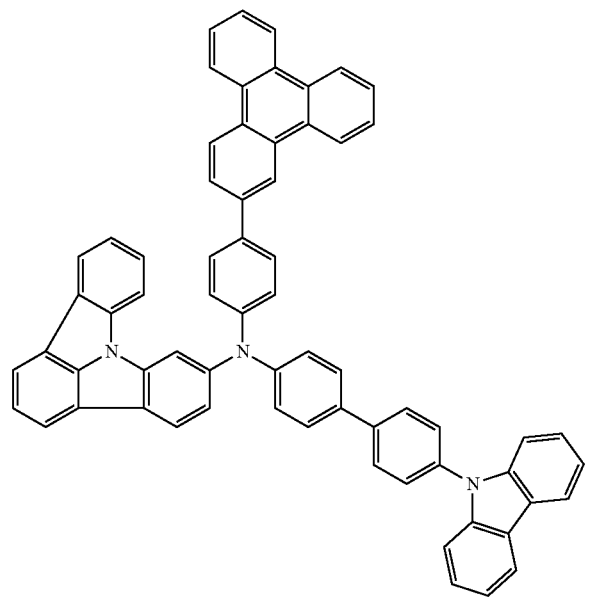
148
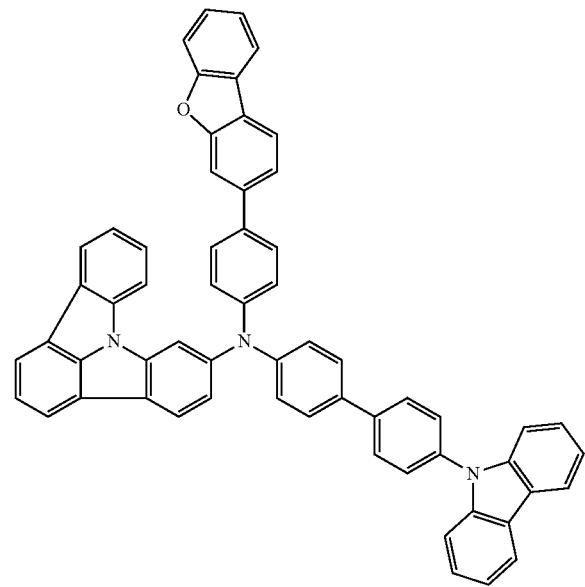
149
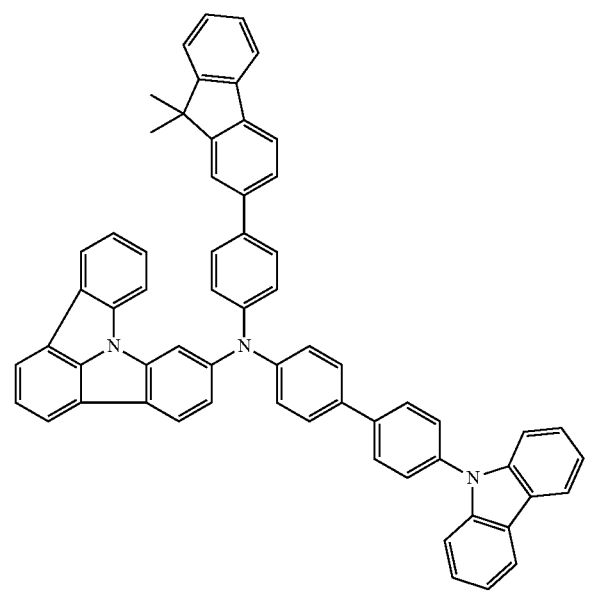
150

-continued
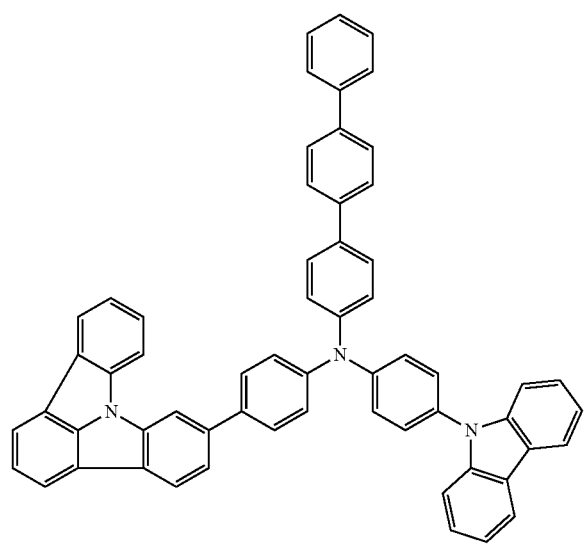
151
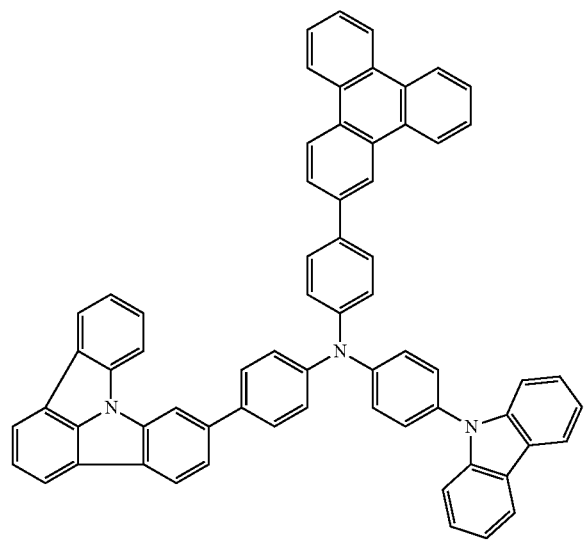
152
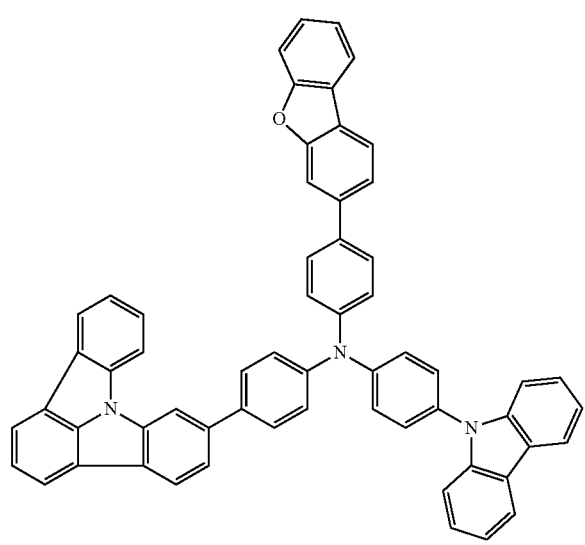
153
The material for an organic EL device according to an example embodiment may include one or more compounds having the following structures.
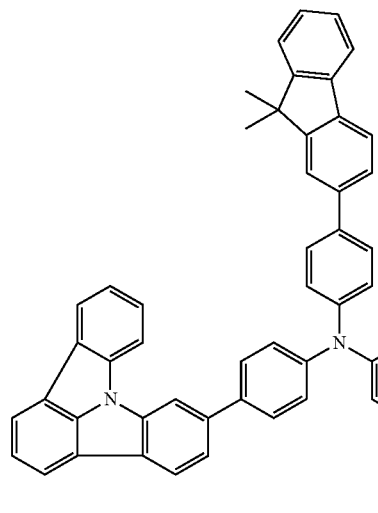
154
155
156

157
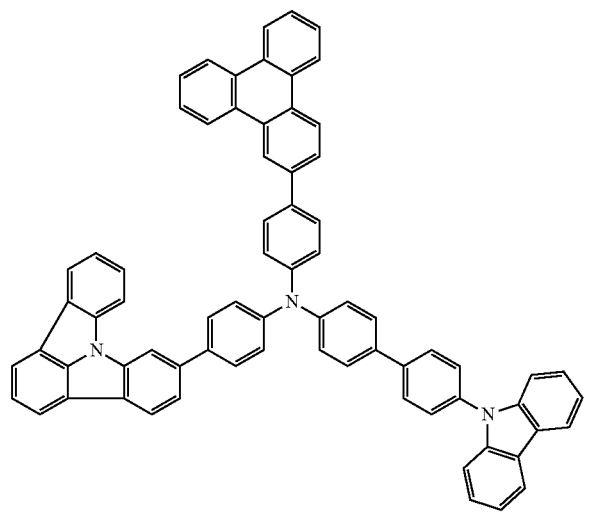
158
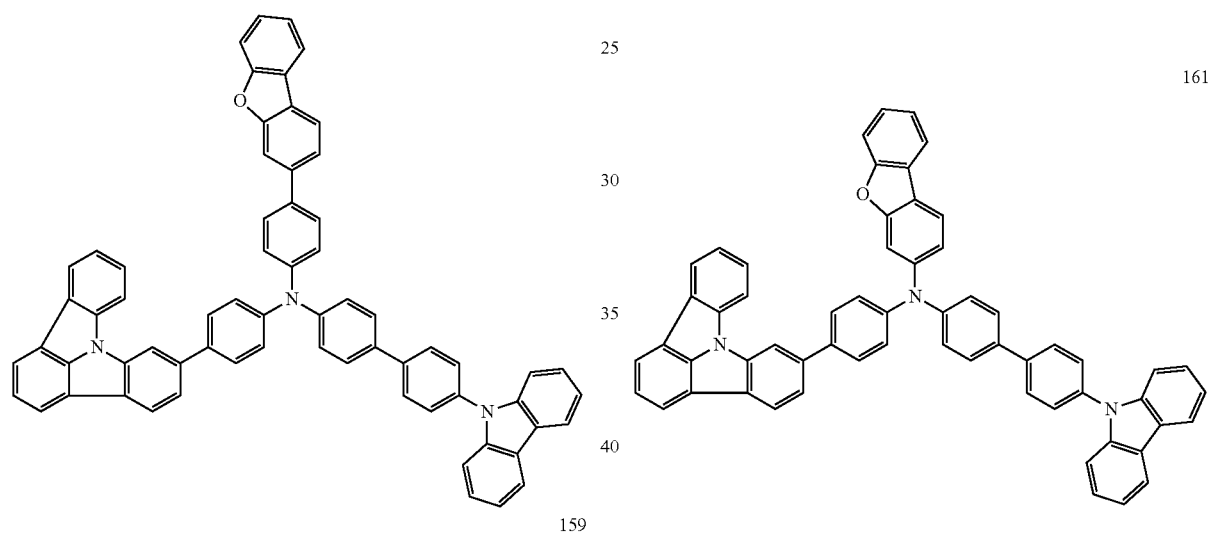
159
160
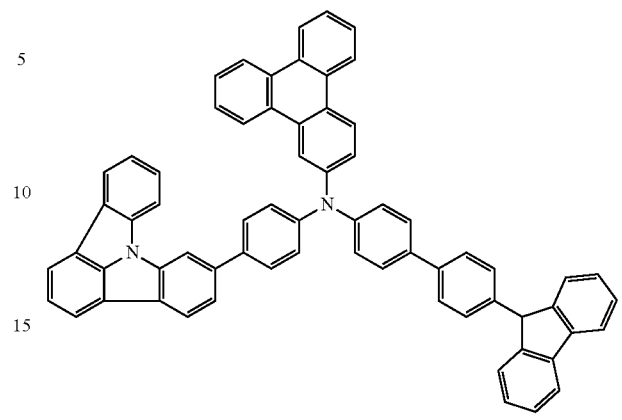
161
162
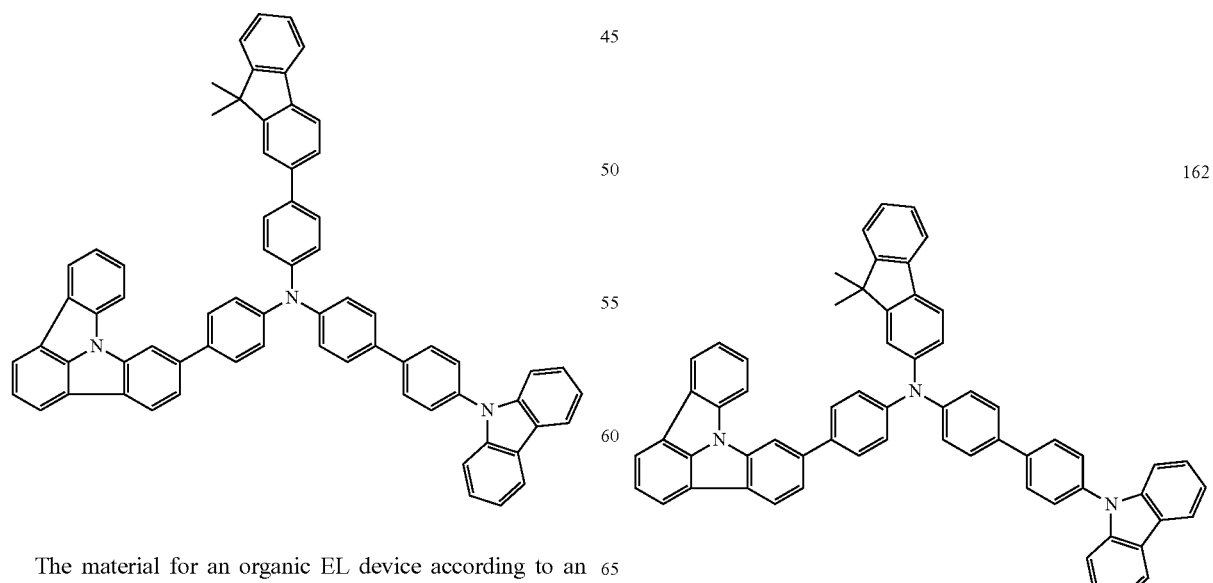
The material for an organic EL device according to an example embodiment may include one or more compounds having the following structures.

163
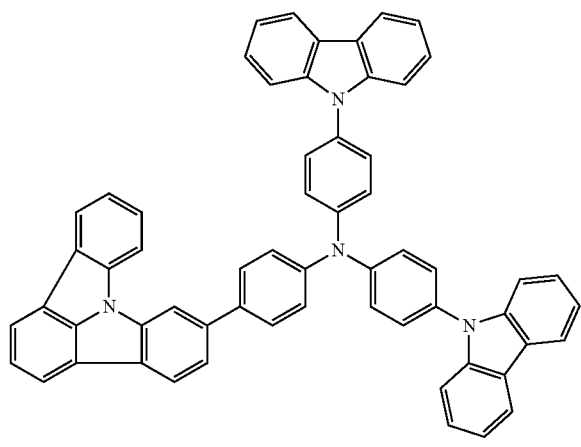
164
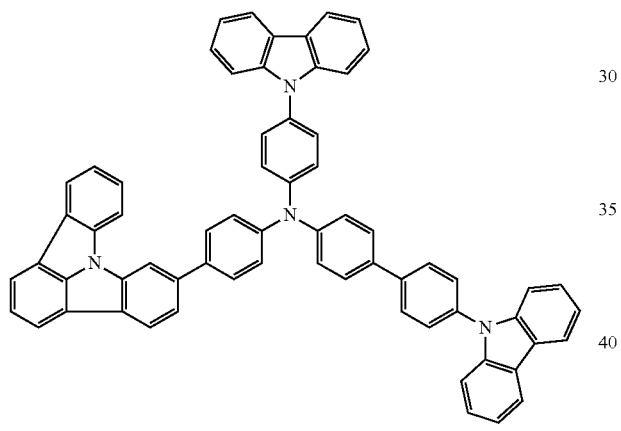
165
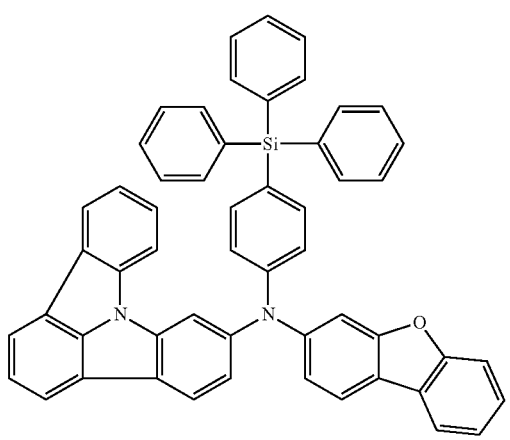
167
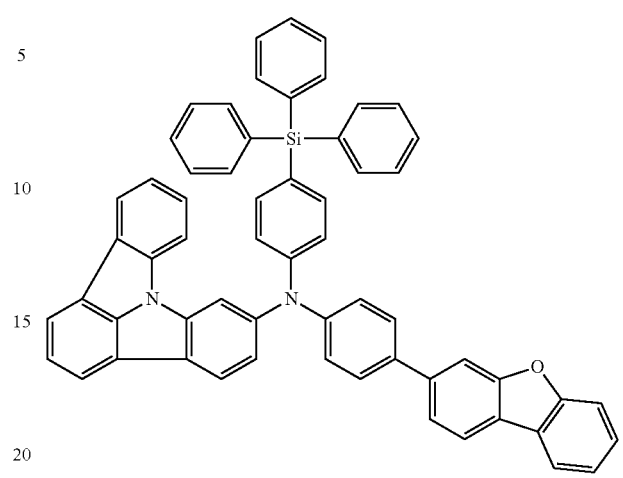
The material for an organic EL device according to an example embodiment may include one or more compounds having the following structures.
168
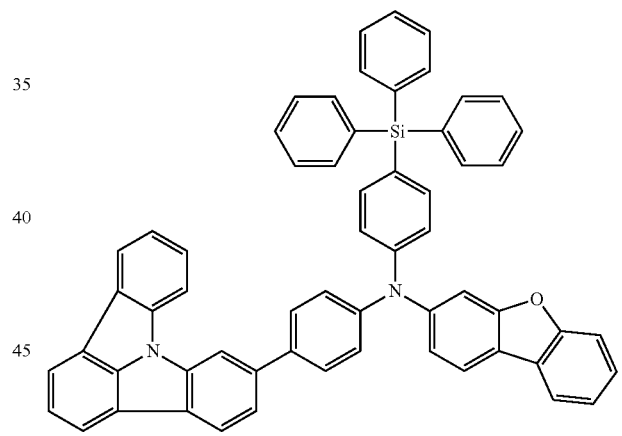
169
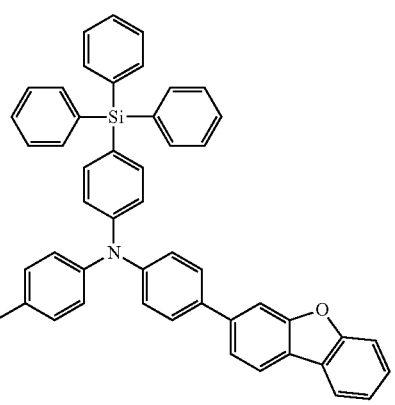

170
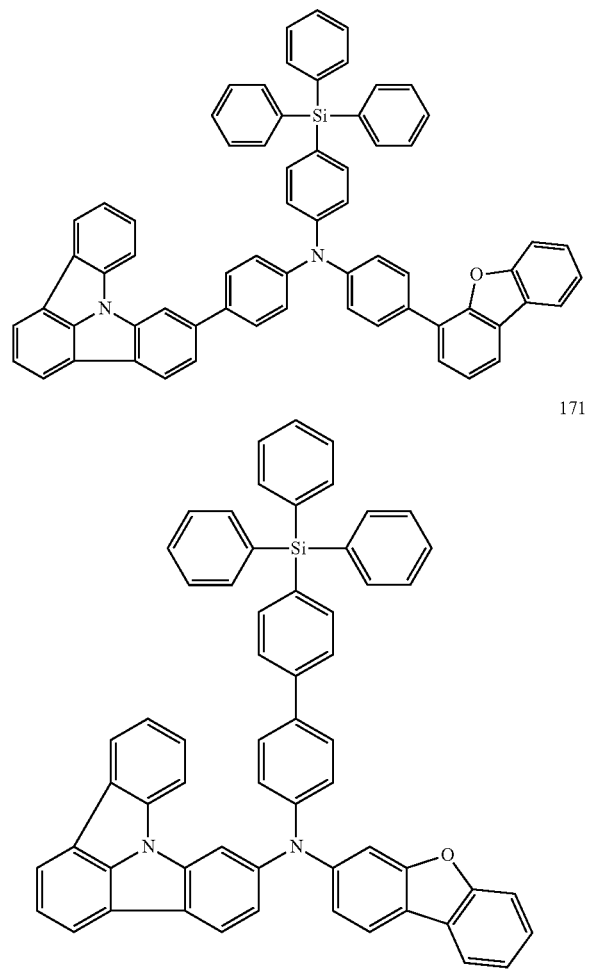
171
172
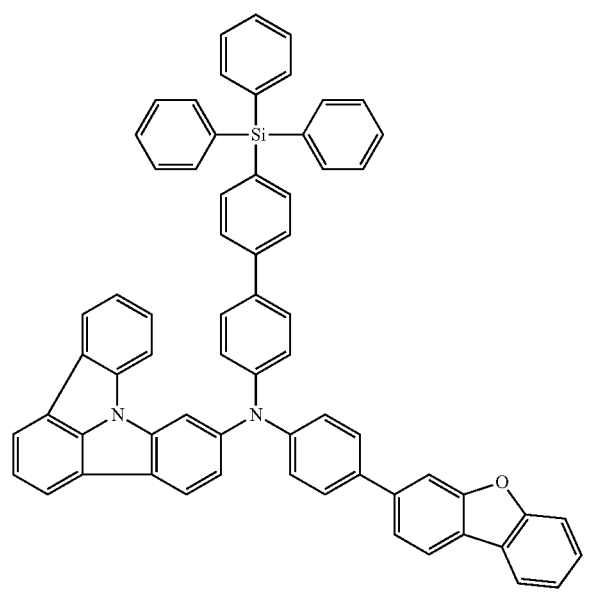
173
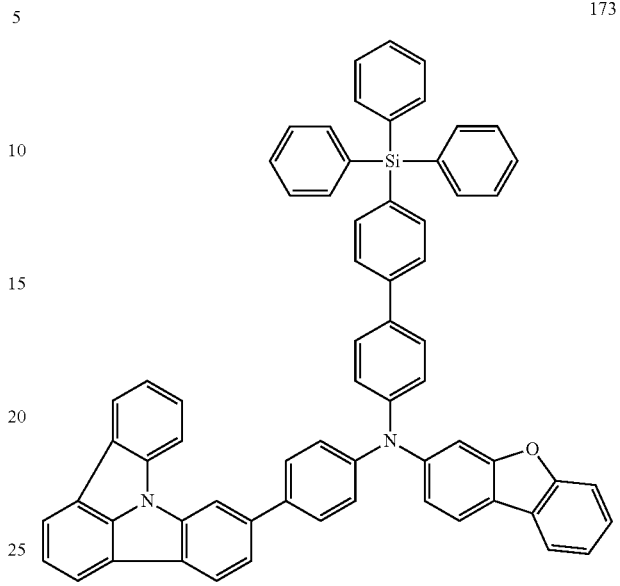
174
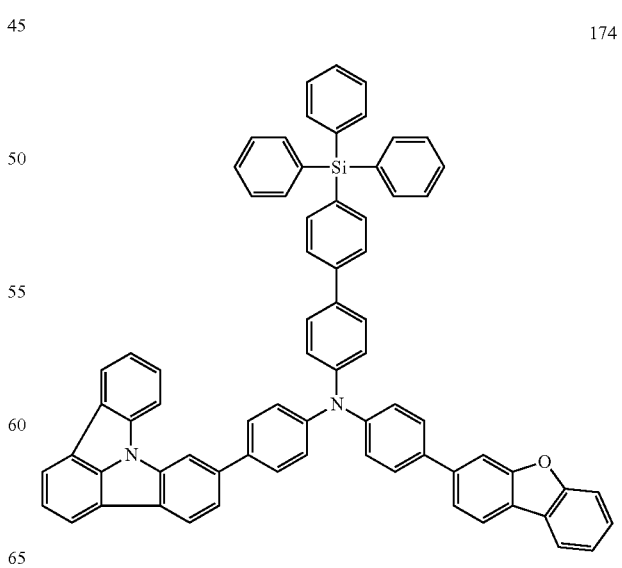

175
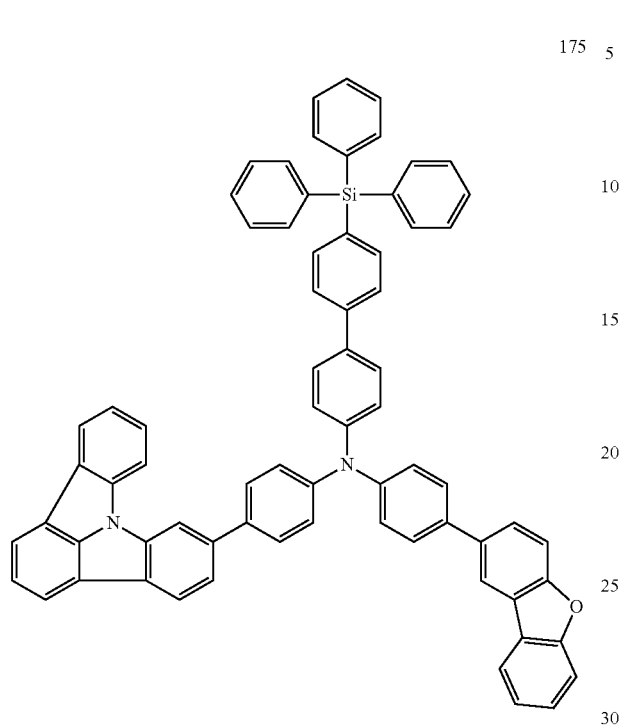
176
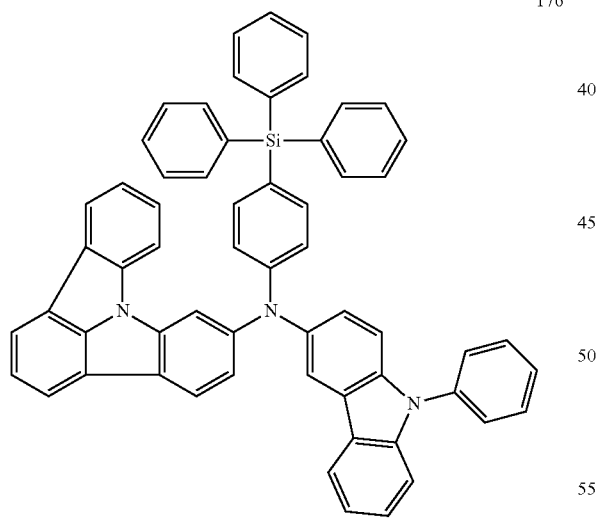
177
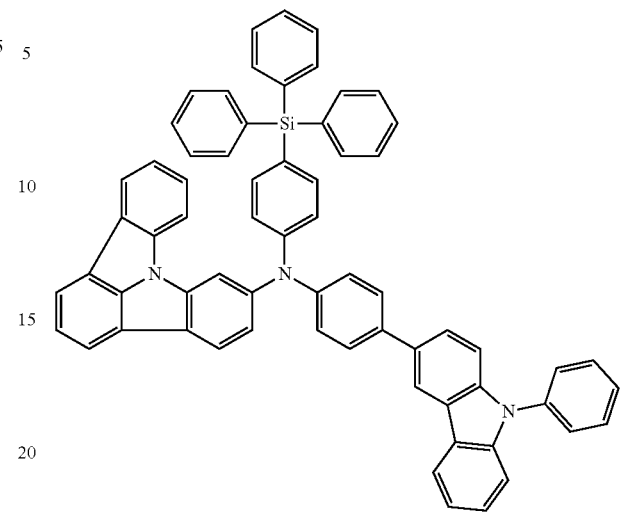
178
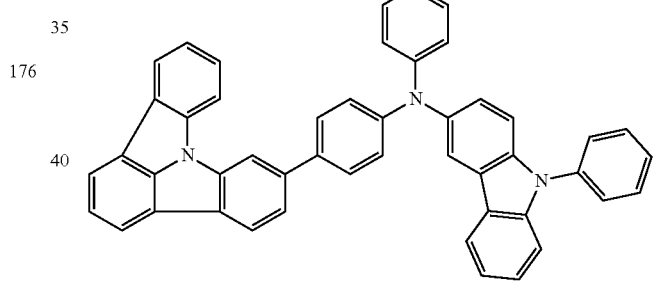
179
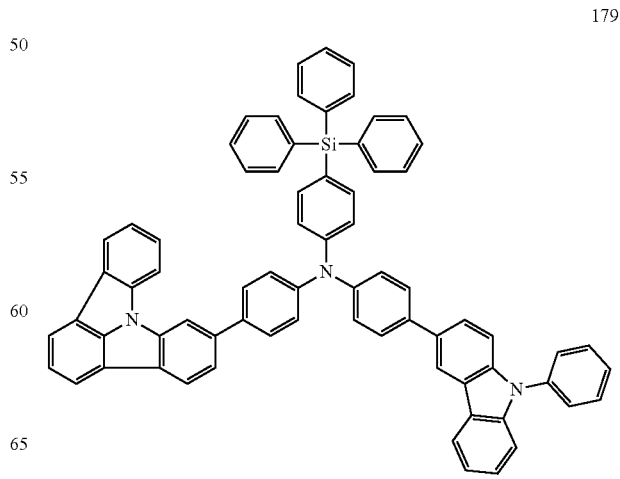
The material for an organic EL device according to an example embodiment may include one or more compounds having the following structures.

180
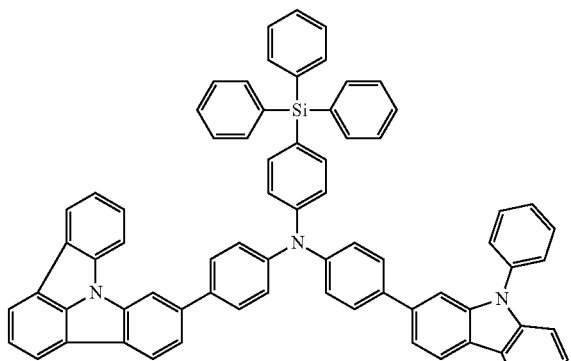
181
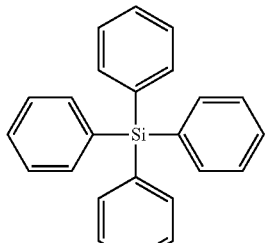
182
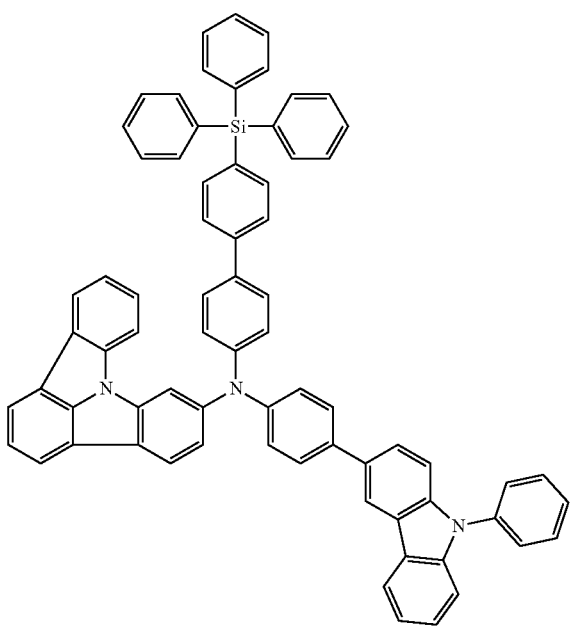
183
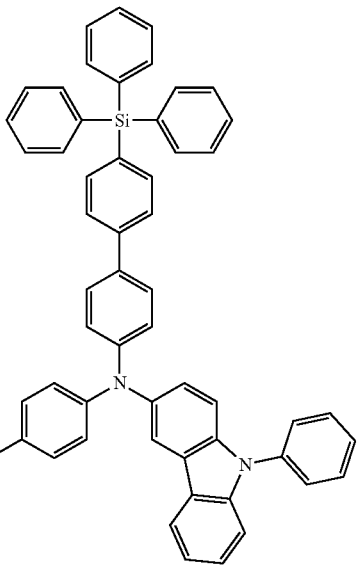
184
The material for an organic EL device according to an example embodiment may include one or more compounds having the following structures.

185
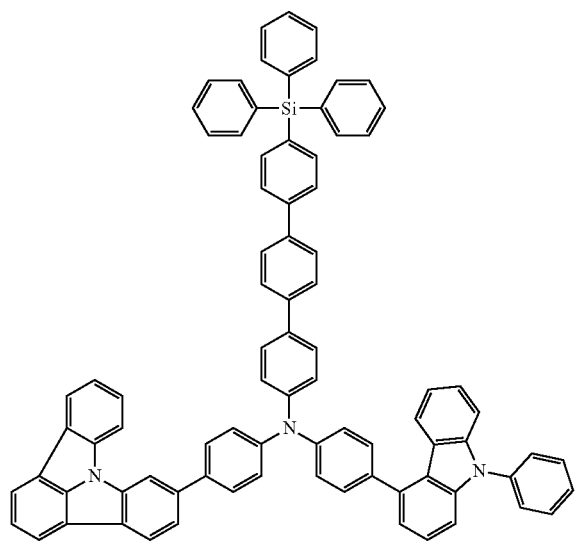
186
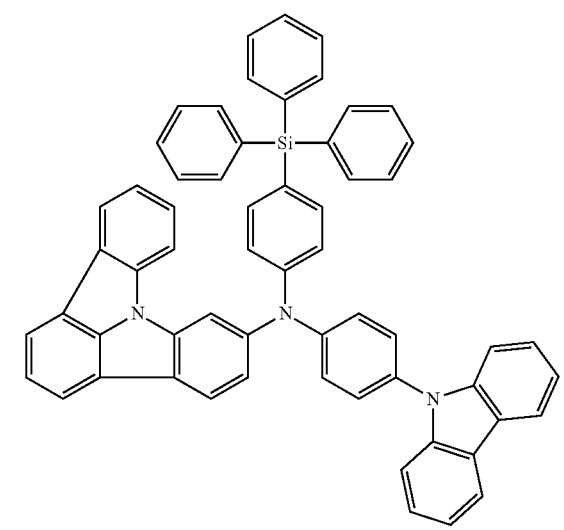
187
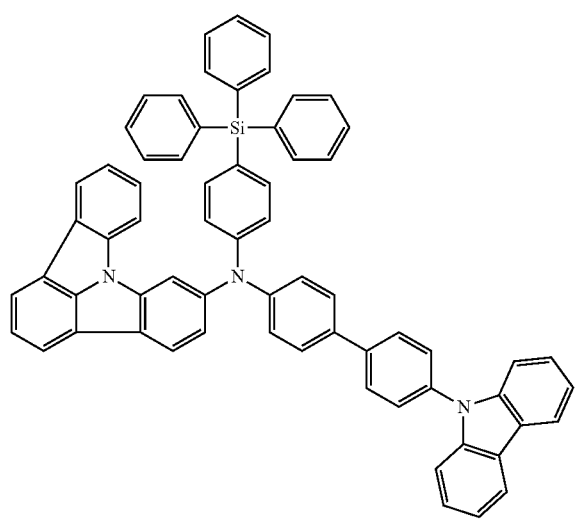
188
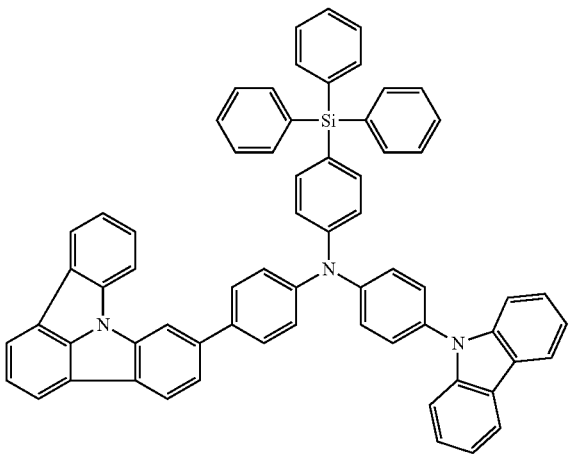
189
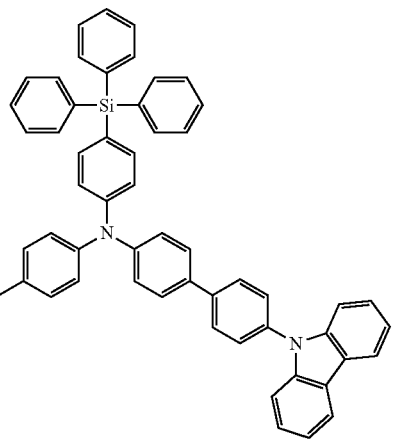
190
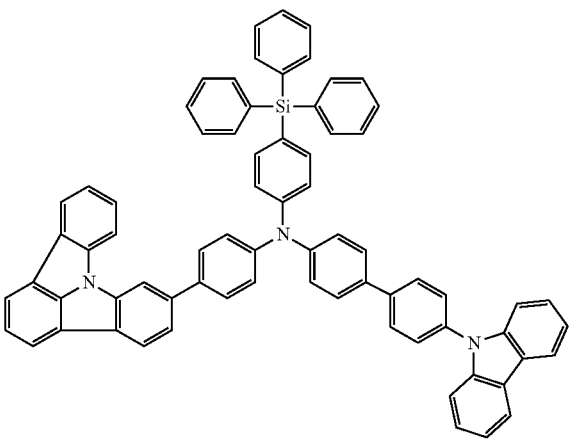

191
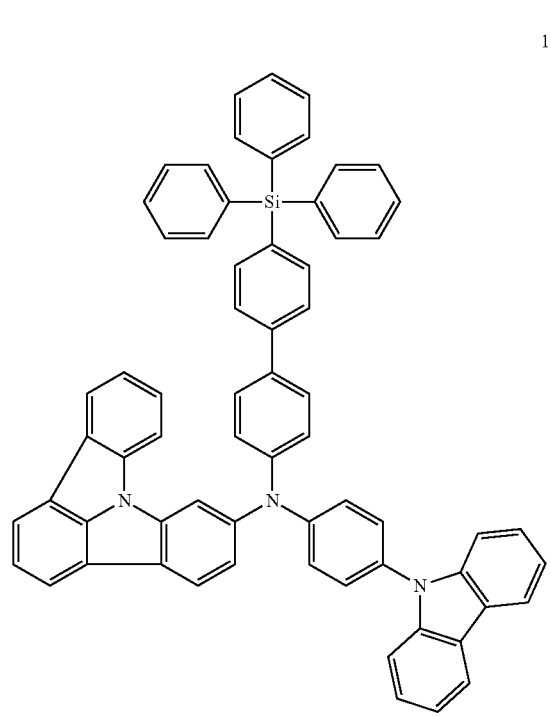
192
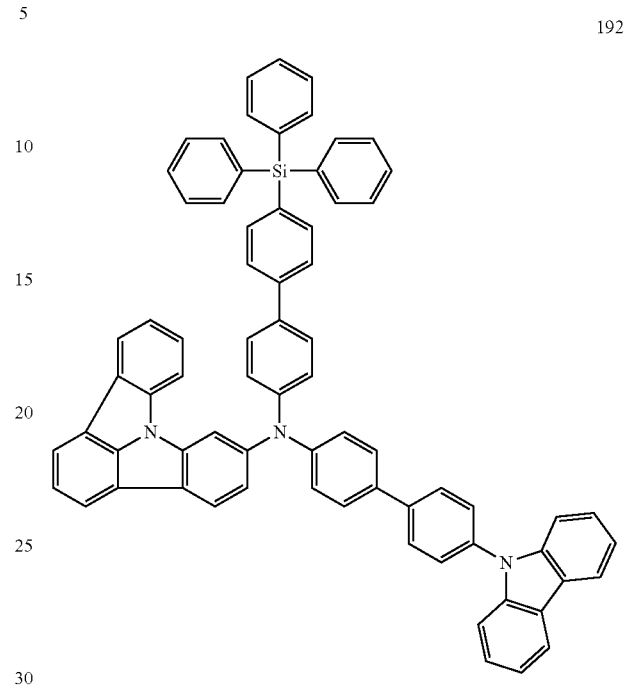
The material for an organic EL device according to an example embodiment may include one or more compounds having the following structures.
193
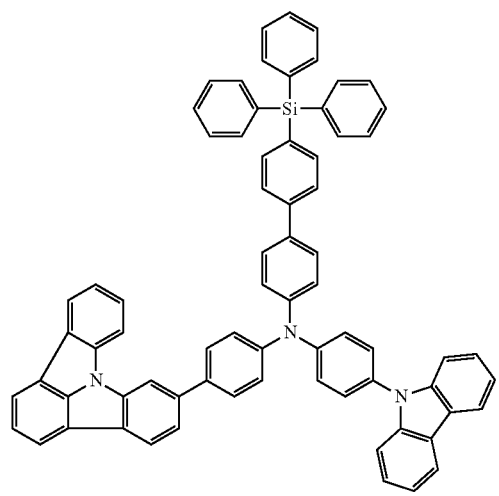
194
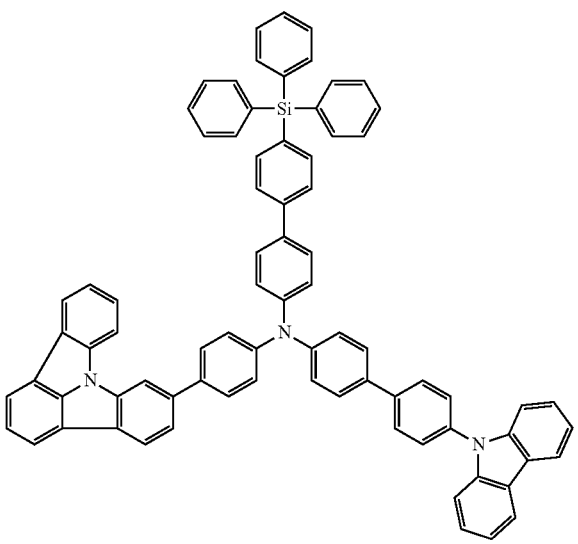

-continued
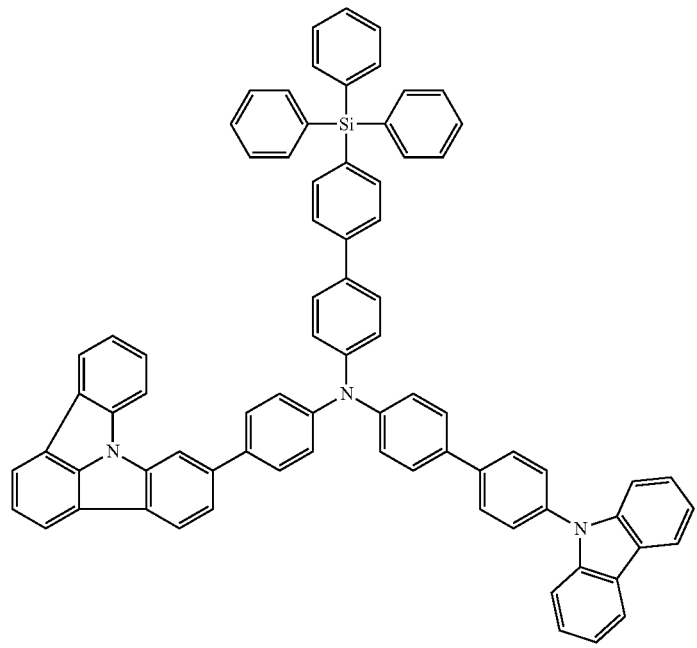
195
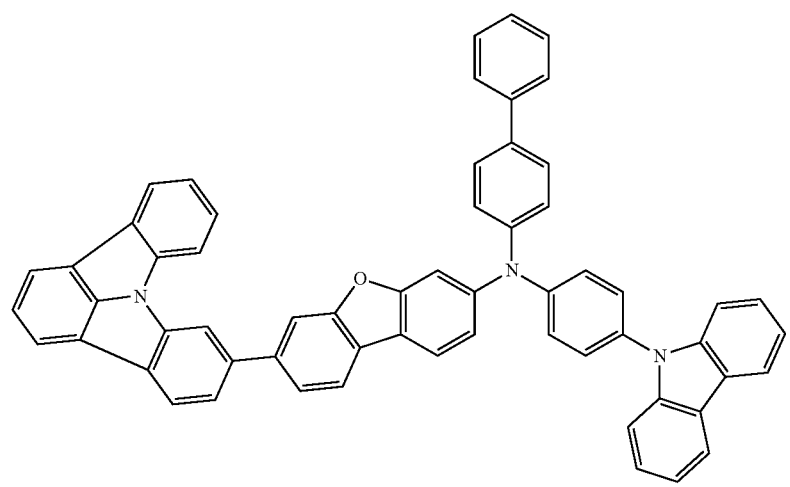
196
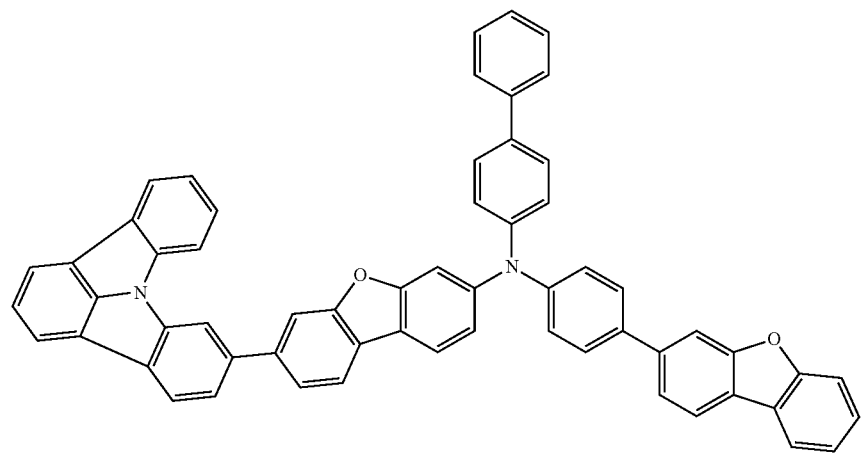
197

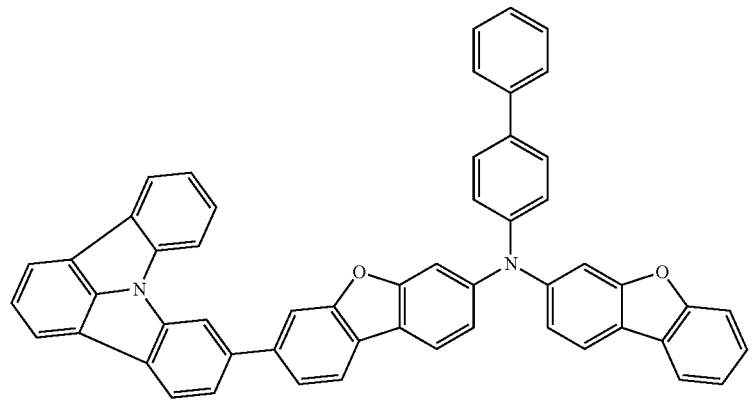
198
The material for an organic EL device according to an example embodiment may include one or more compounds having the following structures.
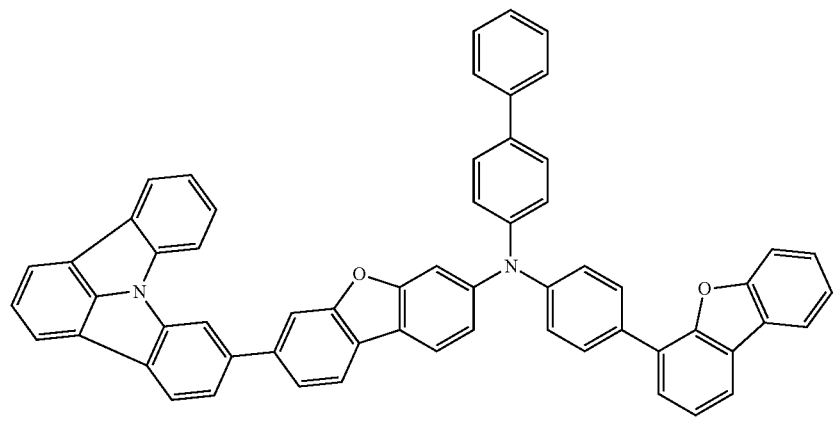
199
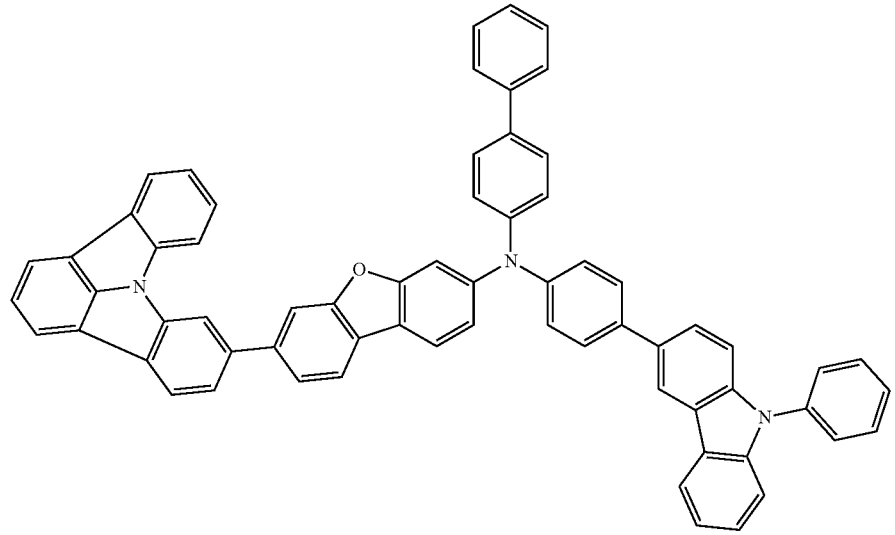
200

-continued
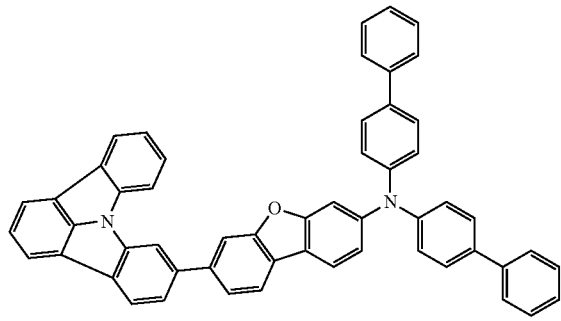
201
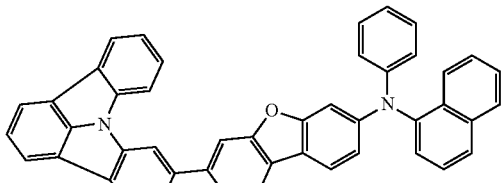
202
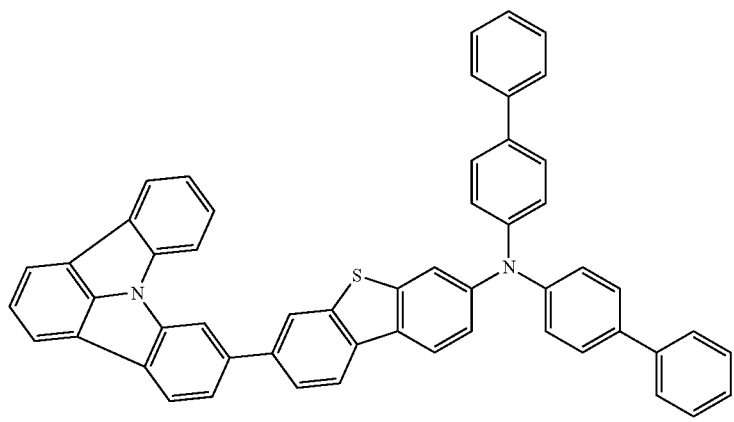
203
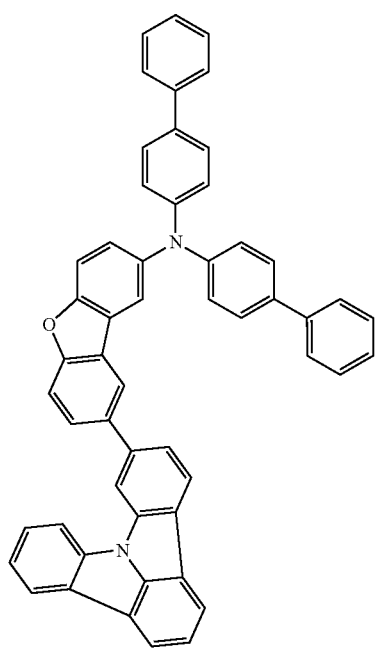
204
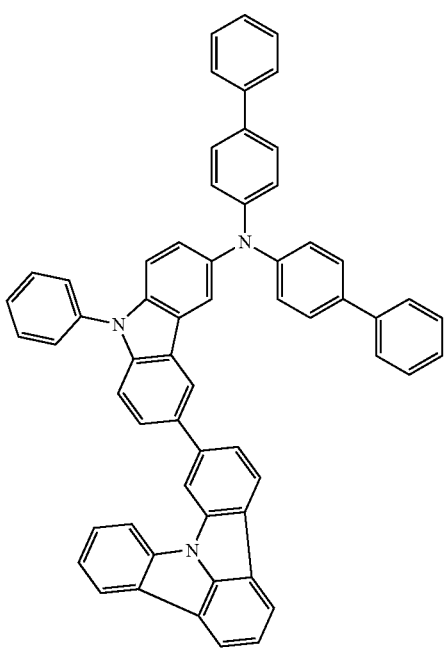
205

The material for an organic EL device according to an example embodiment may include one or more compounds having the following structures.
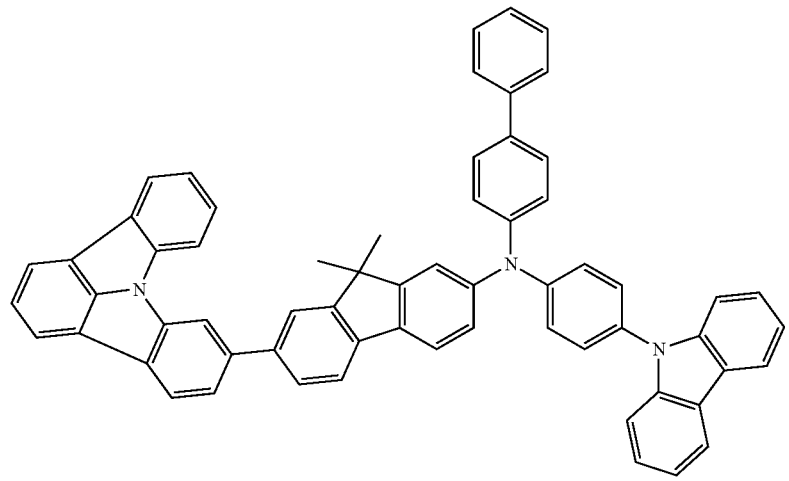
206
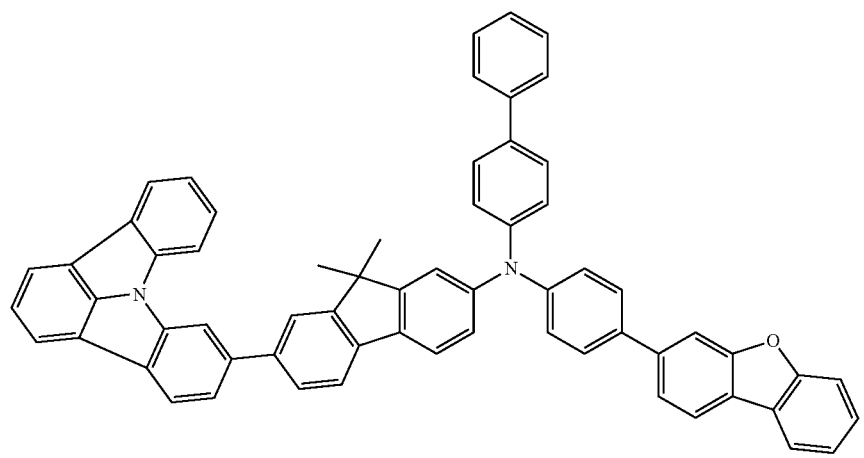
207
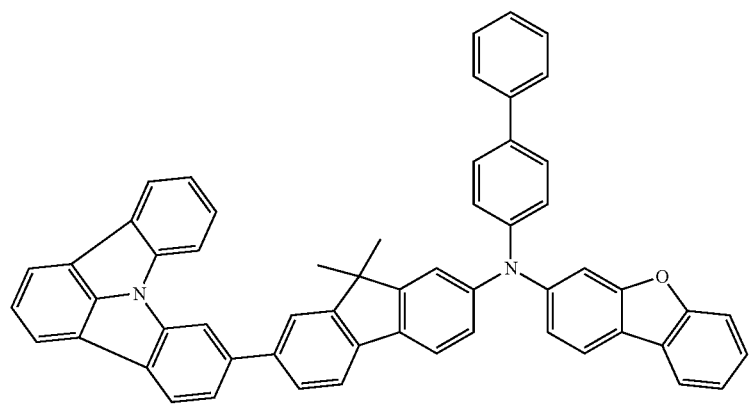
208

209
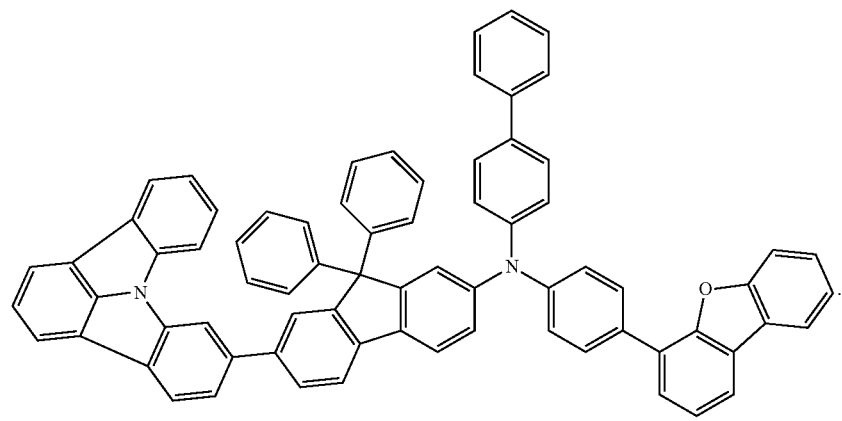
210
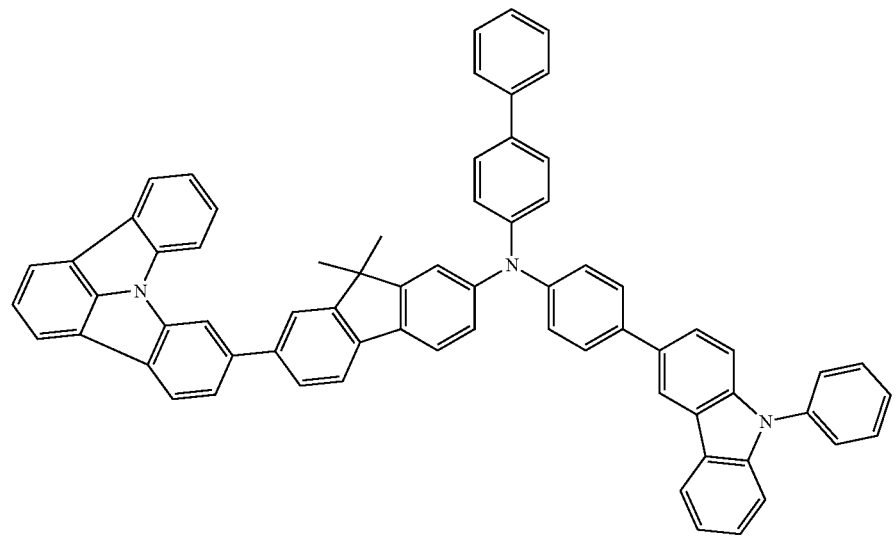
211
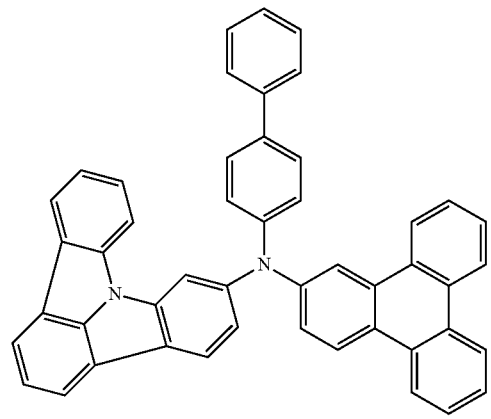

The material for an organic EL device according to an example embodiment may include one or more compounds having the following structures.
212
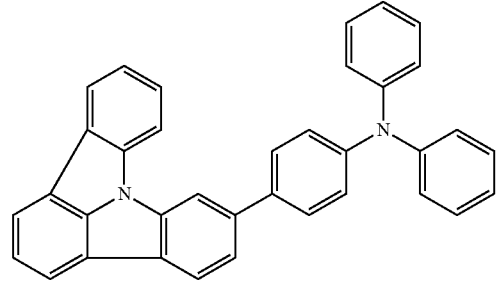
213
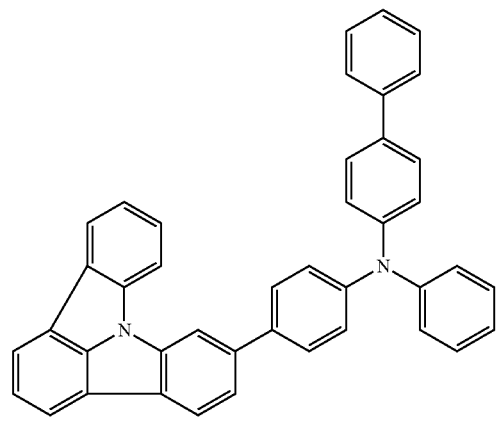
214
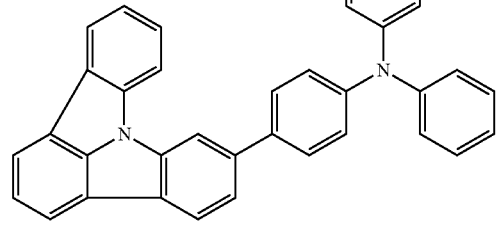
215
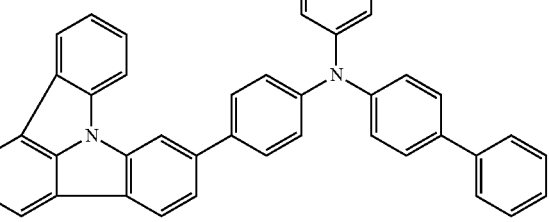
216
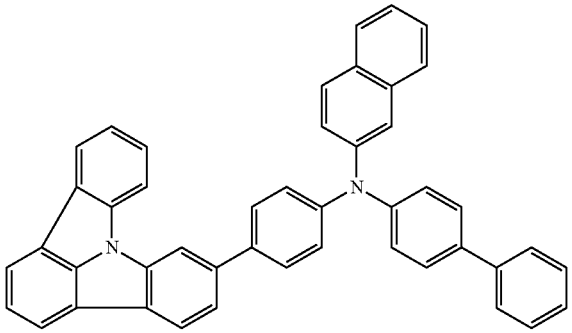
217
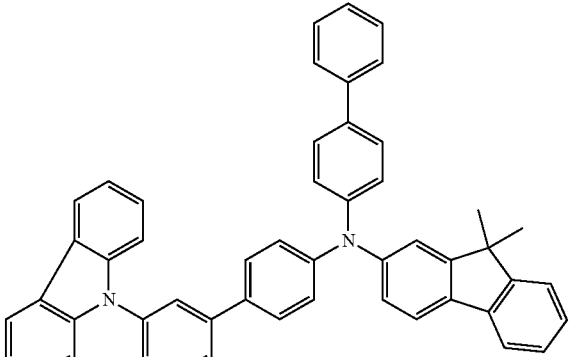
218
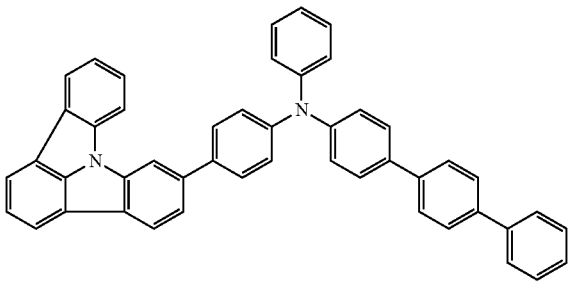
219
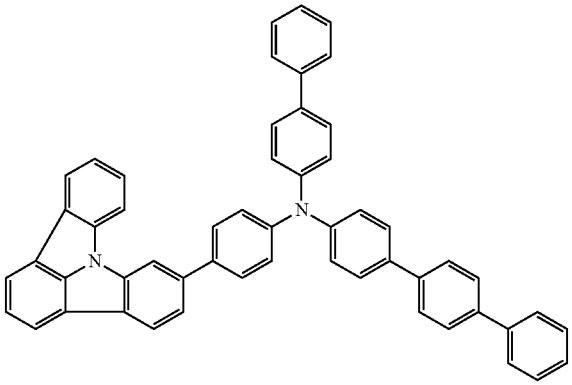
The material for an organic EL device according to an example embodiment may include one or more compounds having the following structures.

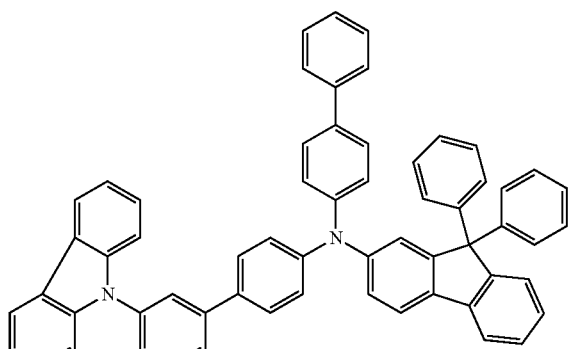
220
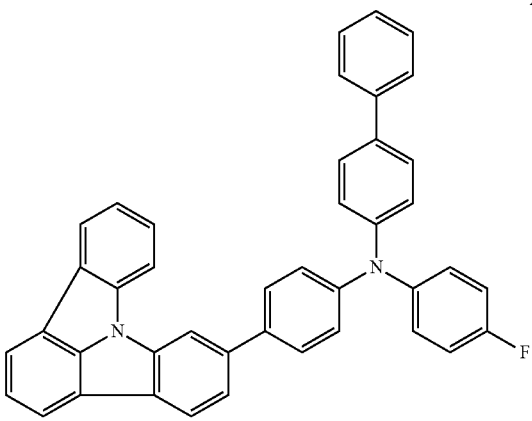
226
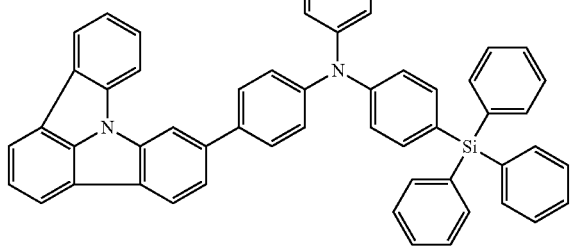
221
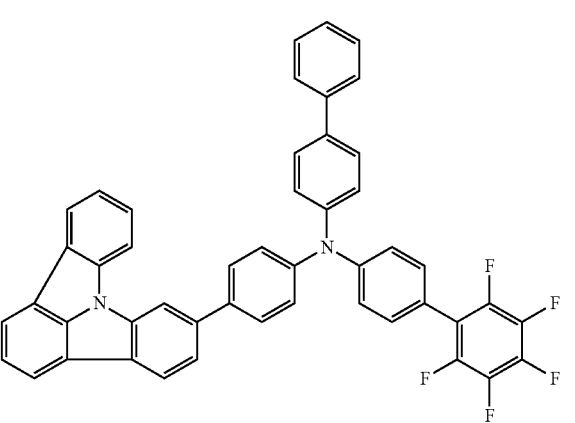
227
224
The material for an organic EL device according to an example embodiment may include one or more compounds having the following structures.
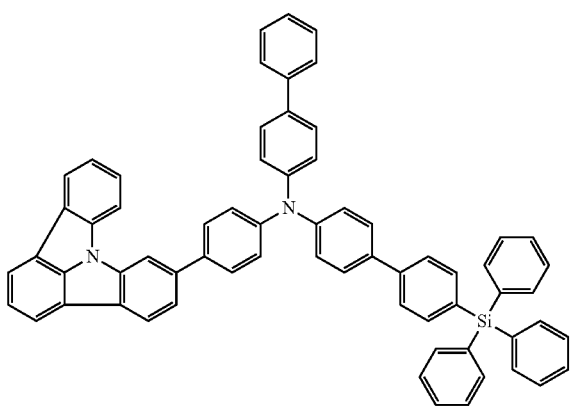
225
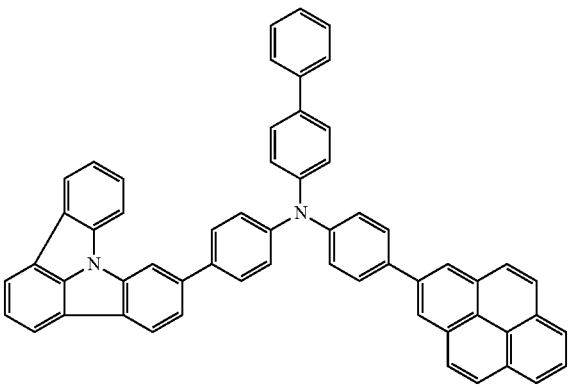
228

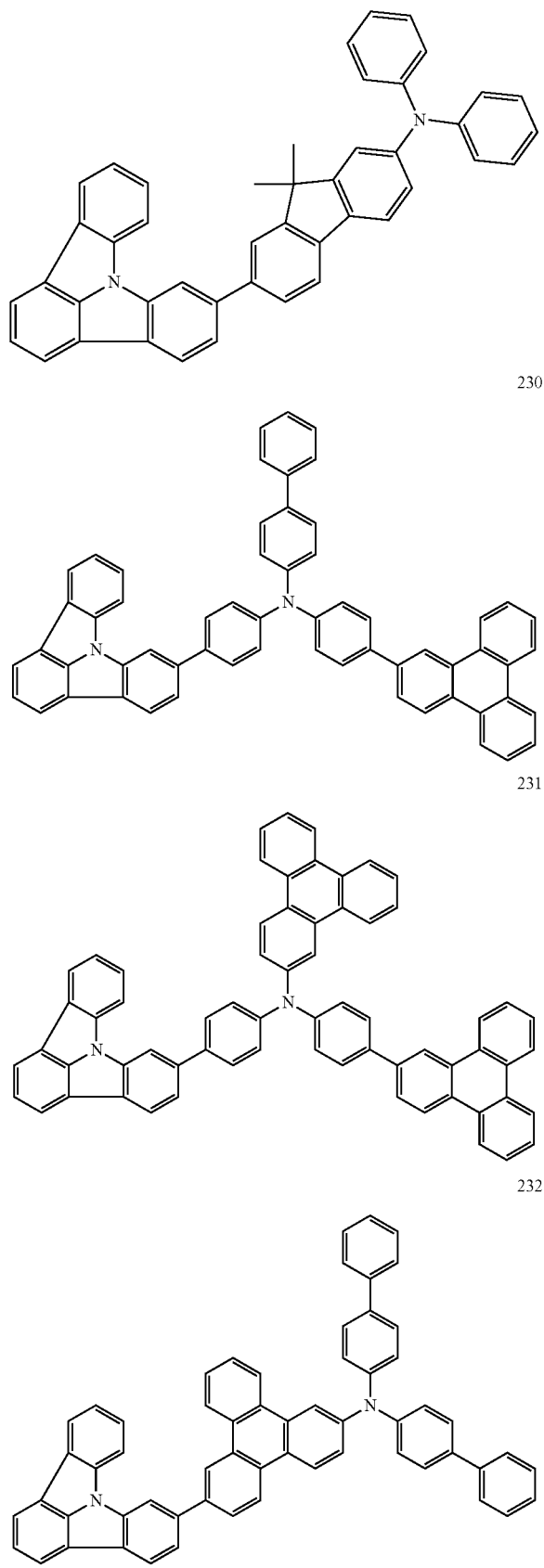

229
230
231
232

The material for an organic EL device according to an example embodiment may be used in a layer, e.g., one of a plurality of stacked layers, disposed between an anode and an emission layer. For example, the material may be used as a hole transport material for an organic EL device. By using the material for an organic EL device according to an example embodiment for the formation of the hole transport layer, an organic EL device having high efficiency and long life may be manufactured.

The material for an organic EL device according to an example embodiment may be used as a hole transport material of the organic EL device or as a material for another layer. For example, the material for an organic EL device according to an example embodiment may be used as the material of the hole injection layer. In the case that the material for an organic EL device according to an example embodiment is used as the material for the hole injection layer, deterioration of the hole injection layer due to electrons may be restrained. Thus, the long life of an organic EL device may be realized as in the case of using the material as the hole transport material. In addition, the diamine derivative according to an example embodiment may have electron tolerance. Thus, the material may be used as a host material of an emission layer.

(Organic EL Device)

An organic EL device using the material for an organic EL device according to an example embodiment will now be explained.

FIG. 1 illustrates a schematic diagram of a configuration of an organic EL device 100 according to an example embodiment.

Referring to FIG. 1, the organic EL device 100 may include, for example, a substrate 102, an anode 104, a hole injection layer 106, a hole transport layer 108, an emission layer 110, an electron transport layer 112, an electron injection layer 114, and a cathode 116. In an embodiment, the material for an organic EL device according to an example embodiment may be used in the hole transport layer.

An example embodiment using the material for an organic EL device according to an example embodiment in the hole transport layer 108 will now be explained. The substrate 102 may be, for example, a transparent glass substrate, a semiconductor substrate formed by using silicon, etc., or a flexible substrate of a resin, etc. The anode 104 is disposed on the substrate 102 and may be formed using, for example, indium tin oxide (ITO), indium zinc oxide (IZO), etc. The hole injection layer 106 is disposed on the anode 104 and may include, for example, 4,4',4''-tris[2-naphthyl)(phenyl)amino]triphenylamine (2-TNATA), N,N,N',N'-tetrakis(3-methylphenyl)-3,3'-dimethylbenzidine (HMTPD), etc. The hole transport layer 108 is disposed on the hole injection layer 106. The hole transport layer 108 may include the compound represented by Formula (1). The hole transport layer 108 may be formed using the material for an organic EL device according to an example embodiment. The emission layer 110 is disposed on the hole transport layer 108. The emission layer 110 may include the compound represented by Formula (1). The emission layer 108 may be formed using the material for an organic EL device according to an example embodiment. In another implementation, the emission layer 110 may be formed using, for example, a host material including 9,10-di(2-naphthyl)anthracene (ADN) doped with 2,5,8,11-tetra-t-butylperylene (TBP). The electron transport layer 112 is disposed on the emission layer 110 and may be formed using, for example, a material including tris(8-hydroxyquinolinato)aluminum ($Alq_3$).

The electron injection layer 114 is disposed on the electron transport layer 112 and may be formed using, for example, a material including lithium fluoride (LiF). The cathode 116 is disposed on the electron injection layer 114 and may be formed using, for example, a metal such as Al or a transparent material such as ITO, IZO, etc. The above-described thin layers may be formed by selecting an appropriate layer forming method such as vacuum deposition, sputtering, various coatings, etc.

In the organic EL device 100 according to the present example embodiment, a hole transport layer possibly realizing high efficiency and long life may be formed by using the material for an organic EL device according to an example embodiment. In addition, the material for an organic EL device according to an example embodiment may be applied in an organic EL apparatus of an active matrix having thin film transistors (TFT).

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Examples

Preparation Method

The material for an organic EL device according to an example embodiment may be synthesized, for example, by the following method.

(Synthesis of Compound 8)

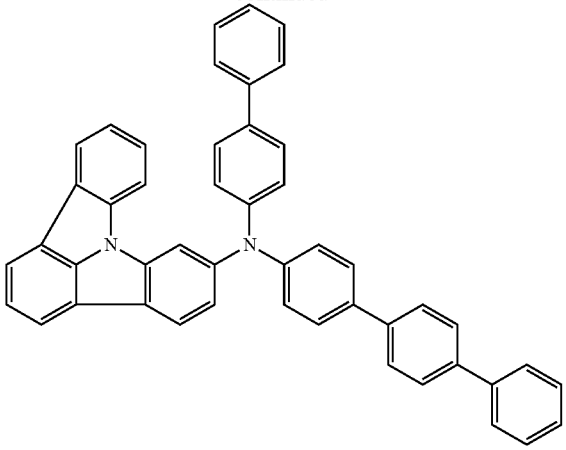

8

An indolocarbazole compound (3.0 mmol), an amine compound (3.0 mmol), a palladium catalyst (0.3 mol), a phosphine ligand (1.2 mol), a basic reagent (12 mmol), and toluene (100 mL) were added in a reaction vessel, followed by charging nitrogen in the vessel and refluxing while stirring for 25 hours. After cooling, water was added in the reactant, and an organic layer was extracted. The organic layer thus obtained was dried with magnesium sulfate anhydrous and filtered, and the filtrate thus obtained was concentrated using a rotary evaporator. The crude product thus obtained was separated by silica gel column chromatography, and the solid thus obtained was recrystallized to produce a target material of Compound 8 as a solid in a powder state with a yield of 35% (APCI+: $C_{48}H_{32}N_2$, measured value 636).

(Synthesis of Compound 14)

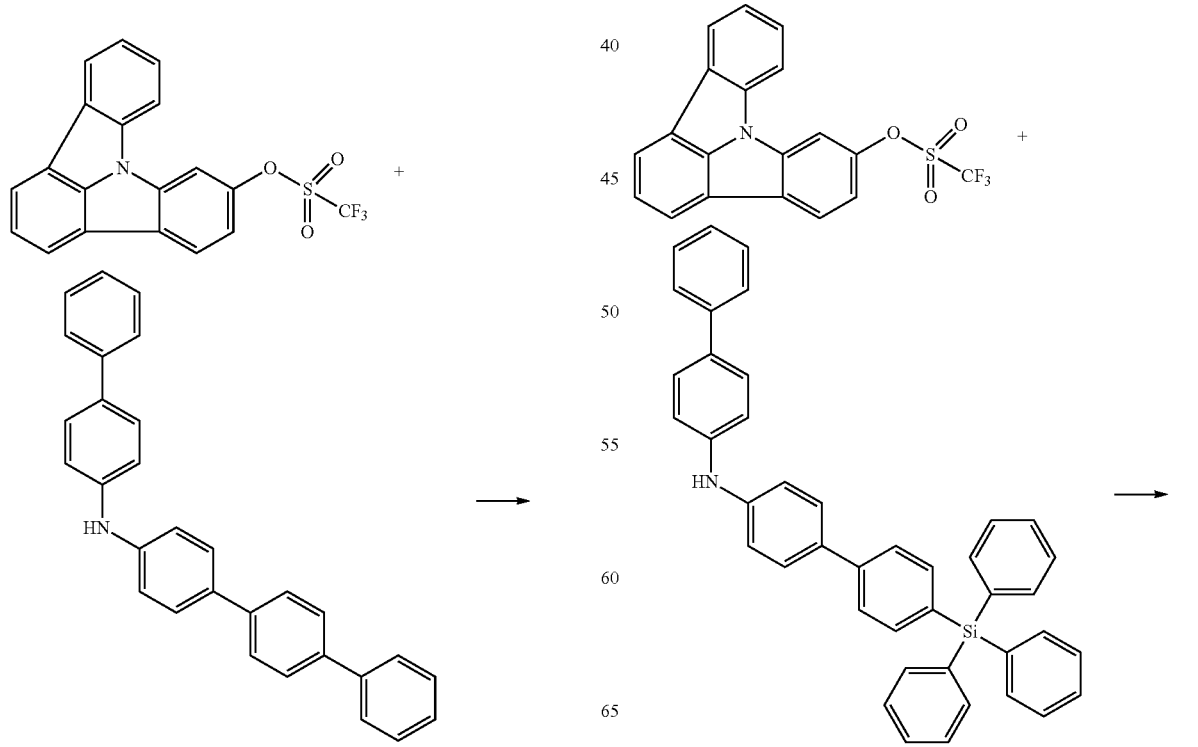

-continued

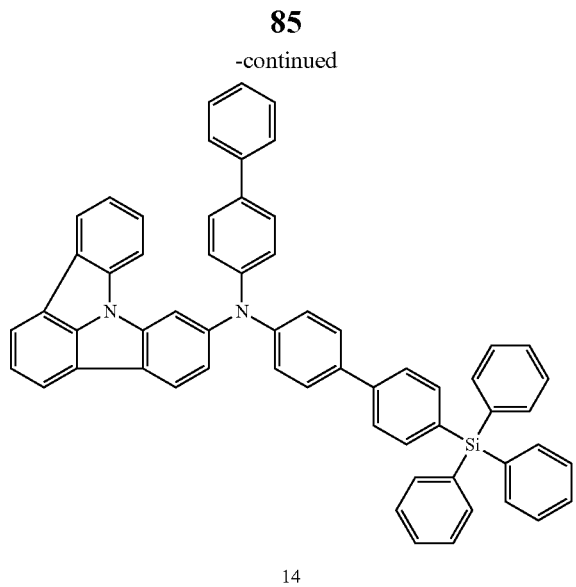

14

An indolocarbazole compound (4.5 mmol), an amine compound (4.5 mmol), a palladium catalyst (0.5 mol), a phosphine ligand (2 mol), a basic reagent (20 mmol), and toluene (150 mL) were added in a reaction vessel, followed by charging nitrogen in the vessel and refluxing while stirring for 20 hours. After cooling, water was added in the reactant, and an organic layer was extracted. The organic layer thus obtained was dried with magnesium sulfate anhydrous and filtered, and the filtrate thus obtained was concentrated using a rotary evaporator. The crude product thus obtained was separated by silica gel column chromatography, and the solid thus obtained was recrystallized to produce a target material of Compound 14 as a solid in a powder state with a yield of 40% (APCI+: $C_{60}H_{42}N_2Si$, measured value 818).

(Synthesis of Compound 214)

-continued

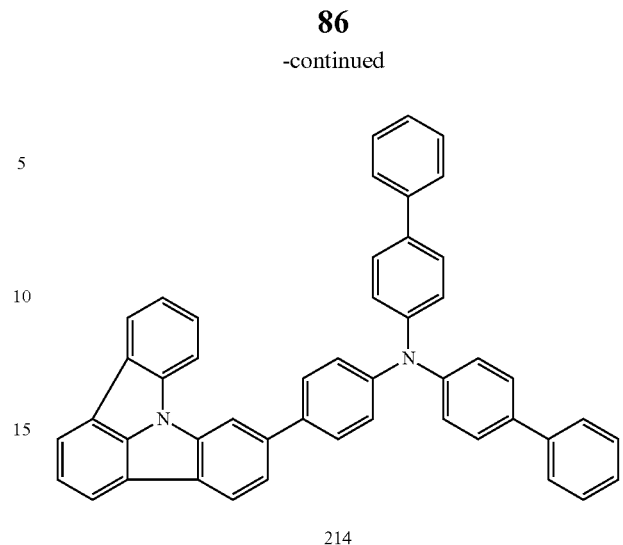

214

An indolocarbazole compound (5.0 mmol), an amine compound (5.0 mmol), a palladium catalyst (0.5 mol), a phosphine ligand (2.0 mol), a basic reagent (20 mmol), toluene (300 mL), water (30 mL) and ethanol (15 mL) were added in a reaction vessel, followed by charging nitrogen in the vessel and refluxing while stirring for 18 hours. After cooling, water was added in the reactant, and an organic layer was extracted. The organic layer thus obtained was dried with magnesium sulfate anhydrous and filtered, and the filtrate thus obtained was concentrated using a rotary evaporator. The crude product thus obtained was separated by silica gel column chromatography, and the solid thus obtained was recrystallized to produce a target material of Compound 214 as a solid in a powder state with a yield of 50% (APCI+: $C_{48}H_{32}N_2$, measured value 636).

(Synthesis of Compound 55)

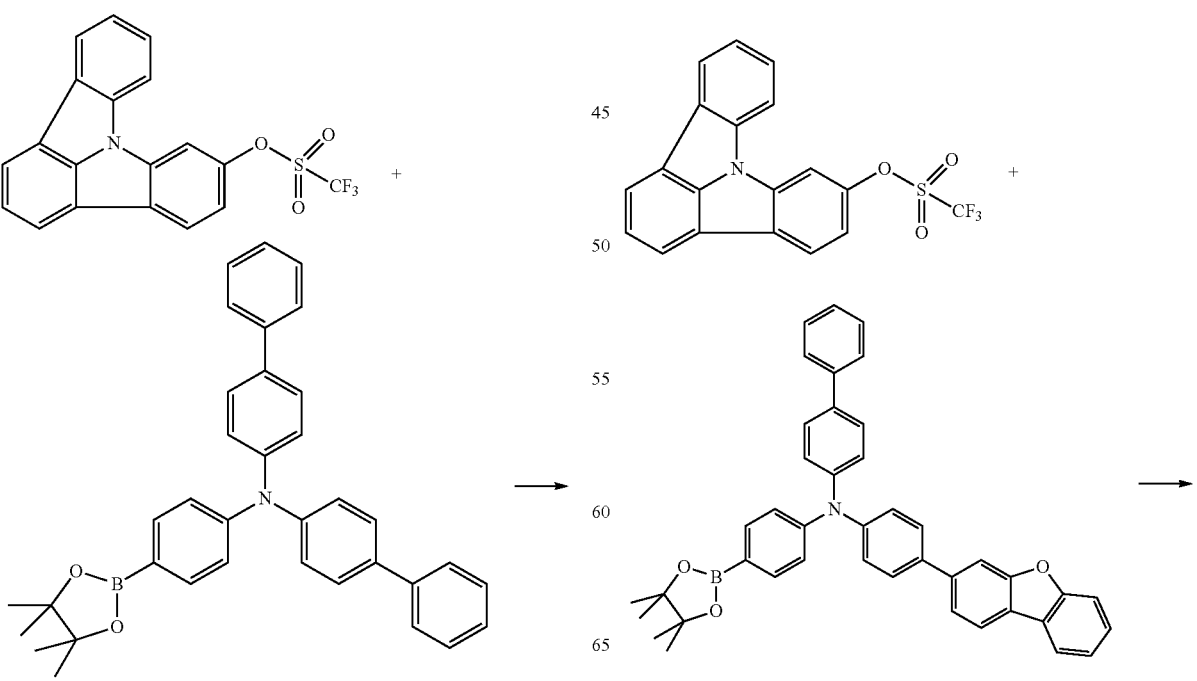

-continued

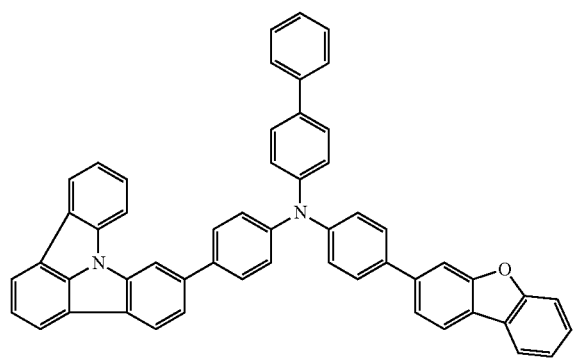

55

An indolocarbazole compound (2.0 mmol), an amine compound (2.0 mmol), a palladium catalyst (0.2 mol), a phosphine ligand (0.8 mol), a basic reagent (8 mmol), toluene (100 mL), water (10 mL) and ethanol (5 mL) were added in a reaction vessel, followed by charging nitrogen in the vessel and refluxing while stirring for 20 hours. After cooling, water was added in the reactant, and an organic layer was extracted. The organic layer thus obtained was dried with magnesium sulfate anhydrous and filtered, and the filtrate thus obtained was concentrated using a rotary evaporator. The crude product thus obtained was separated by silica gel column chromatography, and the solid thus obtained was recrystallized to produce a target material of Compound 55 as a solid in a powder state with a yield of 53% (APCI+: $C_{54}H_{32}N_2O$, measured value 726).

(Synthesis of Compound 224)

-continued

224

An indolocarbazole compound (6.0 mmol), an amine compound (6.0 mmol), a palladium catalyst (0.6 mol), a phosphine ligand (2.4 mol), a basic reagent (24 mmol), toluene (350 mL), water (35 mL) and ethanol (18 mL) were added in a reaction vessel, followed by charging nitrogen in the vessel and refluxing while stirring for 20 hours. After cooling, water was added in the reactant, and an organic layer was extracted. The organic layer thus obtained was dried with magnesium sulfate anhydrous and filtered, and the filtrate thus obtained was concentrated using a rotary evaporator. The crude product thus obtained was separated by silica gel column chromatography, and the solid thus obtained was recrystallized to produce a target material of Compound 224 as a solid in a powder state with a yield of 43% (APCI+: $C_{60}H_{34}N_2Si$, measured value 818).

Organic EL devices according to Examples 1 to 5 were manufactured by using the above Compounds 8, 14, 214, 55, and 224 as hole transport materials. In addition, organic EL devices according to Comparative Examples 1 and 2 were manufactured by using the following Comparative Compounds 251 and 252 as hole transport materials for comparison.

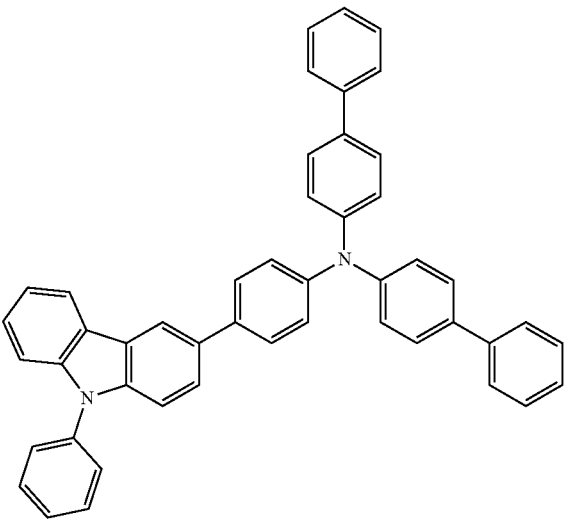

251

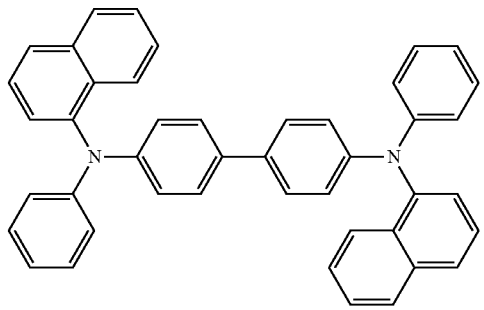

252

In the Examples and Comparative Examples, the substrate 102 was formed by using a transparent glass substrate, the anode 104 was formed using ITO to a thickness of about 150 nm, the hole injection layer 106 was formed using 2-TNATA to a thickness of about 60 nm, the hole transport layer 108 was formed using the compounds according to the Examples and the Comparative Examples to a thickness of about 30 nm, the emission layer 110 was formed using ADN doped with 3% TBP to a thickness of about 25 nm, the electron transport layer 112 was formed using $Alq_3$ to a thickness of about 25 nm, the electron injection layer 114 was formed using LiF to a thickness of about 1 nm, and the cathode 116 was formed using Al to a thickness of about 100 nm.

With respect to the organic EL devices thus manufactured, the voltage, the emission efficiency, and the life were evaluated. The values were measured and evaluated at current density of 10 $mA/cm^2$ and half life of 1,000 $cd/m^2$.

TABLE 1

|  | Voltage (V) | Emission efficiency (cd/A) | Half Life (hr) |
| --- | --- | --- | --- |
| Example 1 | 6.5 | 8.0 | 2,500 |
| Example 2 | 6.8 | 8.8 | 3,000 |
| Example 3 | 6.7 | 8.0 | 2,200 |
| Example 4 | 6.6 | 8.5 | 2,700 |
| Example 5 | 6.9 | 9.2 | 2,800 |
| Comparative Example 1 | 7.5 | 6.2 | 1,500 |
| Comparative Example 2 | 8.1 | 5.3 | 1,200 |

As shown in Table 1, organic EL devices including the amine compound combined at position 6 of the indolo[3,2,1-jk]carbazolyl group exhibited improved emission efficiency and increased half life when compared to an organic EL device of Comparative Example 1 using an amine compound having an carbazolyl group or an organic EL device of Comparative Example 2 using a diamine compound combined with an aryl group.

By way of summation and review, an example of an organic electroluminescence device (organic EL device) is an organic EL device that includes an anode, a hole transport layer disposed on the anode, an emission layer disposed on the hole transport layer, an electron transport layer disposed on the emission layer, and a cathode disposed on the electron transport layer. Holes injected from the anode are injected into the emission layer via the hole transport layer. Meanwhile, electrons are injected from the cathode, and then injected into the emission layer via the electron transport layer. The holes and the electrons injected into the emission layer are recombined to generate excitons within the emission layer. The organic EL device emits light by using light generated during the transition of the excitons to a ground state. The organic EL device may have various forms.

In application of the organic EL device in a display apparatus, high efficiency and long life of the organic EL device are desired, and the normalization, the stabilization, and the durability of a hole transport layer have been studied to realize the high efficiency and long life of the organic EL device. As a material used in a hole transport layer, various compounds such as an aromatic amine-based compound have been studied.

As described above, embodiments relate to a compound for an organic electroluminescence device having high efficiency in a blue emission region and a green emission region, and an organic electroluminescence device including the same. Embodiments may provide a material of an organic EL device having high efficiency and long life, and an organic EL device including the same.

The material for an organic EL device according to an example embodiment is an amine compound combined at position 6 of an indolo[3,2,1-jk]carbazolyl group, which has a high electron tolerance, greater than that of a carbazolyl group, and thus an organic EL device having high efficiency and long life may be manufactured.

According to an example embodiment, an amine compound combined at position 6 of an indolo[3,2,1-jk]carbazolyl group via a single bond or a connecting group, such as a substituted or unsubstituted aryl group having 6 to 18 ring carbon atoms, is used as the material for an organic EL device, and an organic EL device having high efficiency and long life may be manufactured.

In an example embodiment, a hole transport material includes the material for an organic EL device according to an embodiment.

According to an example embodiment, an organic EL device having high efficiency and long life may be manufactured by using an amine compound combined at position 6 of an indolo[3,2,1-jk]carbazolyl group (having greater n plane when compared to that of a carbazolyl group) as a hole transport material.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic electroluminescence (EL) device, the compound being represented by the following Formula (1):

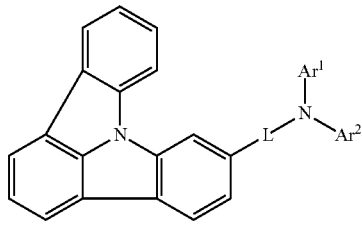

(1)

where Ar¹ and Ar² are independently a substituted or unsubstituted alkyl group, a substituted or unsubstituted aryl group, or a substituted or unsubstituted heteroaryl group, and L is a single bond, a substituted or unsubstituted arylene group, or a substituted or unsubstituted heteroarylene group, and wherein Ar¹ and Ar² are different from each other.

2. The compound as claimed in claim 1, wherein one of Ar¹ and Ar² is a substituted or unsubstituted carbazolyl group, a substituted or unsubstituted dibenzofuryl group, or a substituted or unsubstituted dibenzothienyl group.

3. The compound as claimed in claim 1, wherein one of Ar¹ and Ar² is a substituted or unsubstituted aryl group having 6 to 24 ring carbon atoms.

4. The compound as claimed in claim 1, wherein one of Ar¹ and Ar² is a substituted or unsubstituted carbazolyl group, a substituted or unsubstituted dibenzofuryl group, or a substituted or unsubstituted dibenzothienyl group.

5. The compound as claimed in claim 1, wherein L is a single bond or a substituted or unsubstituted arylene group having 6 to 18 ring carbon atoms.

6. A hole transport material comprising the compound as claimed in claim 1.

7. An organic electroluminescence (EL) device comprising the compound as claimed in claim 1 in a layer disposed between an emission layer and an anode.

8. A compound for an organic electroluminescence (EL) device, the compound being represented by the following Formula (1):

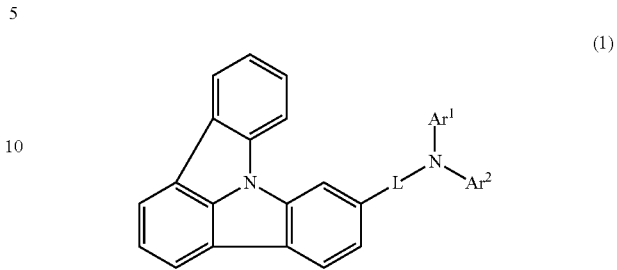

wherein Ar¹ and Ar² are independently a substituted or unsubstituted alkyl group, a substituted or unsubstituted aryl group, or a substituted or unsubstituted heteroaryl group, and L is a single bond, a substituted or unsubstituted arylene group, or a substituted or unsubstituted heteroarylene group, at least one of Ar¹ and Ar² being a substituted or unsubstituted carbazolyl group, a substituted or unsubstituted dibenzofuryl group, or a substituted or unsubstituted dibenzothienyl group.

9. The compound as claimed in claim 8, wherein at least one of Ar¹ and Ar² is a substituted or unsubstituted aryl group having 6 to 24 ring carbon atoms.

10. The compound as claimed in claim 8, wherein L is a single bond or a substituted or unsubstituted arylene group having 6 to 18 ring carbon atoms.

11. A hole transport material comprising the compound as claimed in claim 8.

12. An organic electroluminescence (EL) device comprising the compound as claimed in claim 8 in a layer disposed between an emission layer and an anode.

* * * * *